(12) United States Patent
Lewis et al.

(10) Patent No.: US 8,928,558 B2
(45) Date of Patent: *Jan. 6, 2015

(54) GAZE DETECTION IN A SEE-THROUGH, NEAR-EYE, MIXED REALITY DISPLAY

(71) Applicant: Microsoft Corporation, Redmond, WA (US)

(72) Inventors: John R. Lewis, Bellevue, WA (US); Yichen Wei, Beijing (CN); Robert L. Crocco, Seattle, WA (US); Benjamin I. Vaught, Seattle, WA (US); Alex Aben-Athar Kipman, Redmond, WA (US); Kathryn Stone Perez, Kirkland, WA (US)

(73) Assignee: Microsoft Corporation, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/941,439

(22) Filed: Jul. 12, 2013

(65) Prior Publication Data

US 2013/0300653 A1 Nov. 14, 2013

Related U.S. Application Data

(63) Continuation of application No. 13/221,739, filed on Aug. 30, 2011, now Pat. No. 8,487,838, which is a continuation of application No. 13/844,453, filed on Mar. 15, 2013.

(30) Foreign Application Priority Data

Aug. 29, 2011 (CA) ..................................... 2750287

(51) Int. Cl.
*G09G 5/00* (2006.01)
*G06F 3/01* (2006.01)
(Continued)

(52) U.S. Cl.
CPC ............... *G06F 3/013* (2013.01); *A61B 3/113* (2013.01); *G02B 27/017* (2013.01);
(Continued)

(58) Field of Classification Search
USPC .................. 345/7, 8, 9, 156; 359/630; 396/51
See application file for complete search history.

(56) References Cited

U.S. PATENT DOCUMENTS

| 4,634,384 A | 1/1987 | Neves et al. |
| 4,680,802 A | 7/1987 | Nishida et al. |

(Continued)

FOREIGN PATENT DOCUMENTS

| CA | 2685976 A1 | 11/2008 |
| CN | 1771454 A | 5/2006 |

(Continued)

OTHER PUBLICATIONS

Notice of Allowance and Fee(s) Due dated Dec. 12, 2012, U.S. Appl. No. 13/221,739, filed Aug. 30, 2011, 11 pages.

(Continued)

*Primary Examiner* — Koosha Sharifi-Tafreshi

(74) *Attorney, Agent, or Firm* — Micah Goldsmith; Judy Yee; Micky Minhas

(57) ABSTRACT

The technology provides various embodiments for gaze determination within a see-through, near-eye, mixed reality display device. In some embodiments, the boundaries of a gaze detection coordinate system can be determined from a spatial relationship between a user eye and gaze detection elements such as illuminators and at least one light sensor positioned on a support structure such as an eyeglasses frame. The gaze detection coordinate system allows for determination of a gaze vector from each eye based on data representing glints on the user eye, or a combination of image and glint data. A point of gaze may be determined in a three-dimensional user field of view including real and virtual objects. The spatial relationship between the gaze detection elements and the eye may be checked and may trigger a re-calibration of training data sets if the boundaries of the gaze detection coordinate system have changed.

20 Claims, 21 Drawing Sheets

(51) Int. Cl.
*A61B 3/113* (2006.01)
*G02B 27/01* (2006.01)
*G02B 27/22* (2006.01)
*G02B 27/00* (2006.01)

(52) U.S. Cl.
CPC ........ *G02B 27/2228* (2013.01); *G02B 27/0093* (2013.01); *G02B 2027/0138* (2013.01); *G02B 2027/014* (2013.01); *G02B 2027/0187* (2013.01)
USPC ................... 345/8; 345/9; 359/13; 359/630

(56) References Cited

U.S. PATENT DOCUMENTS

| | | |
|---|---|---|
| 5,016,282 A | 5/1991 | Tomono et al. |
| 5,471,542 A | 11/1995 | Ragland |
| 5,557,364 A | 9/1996 | Shindo et al. |
| 5,689,619 A | 11/1997 | Smyth |
| 5,708,449 A | 1/1998 | Heacock et al. |
| 5,861,940 A | 1/1999 | Robinson et al. |
| 5,886,822 A | 3/1999 | Spitzer |
| 6,034,653 A | 3/2000 | Robertson et al. |
| 6,055,110 A | 4/2000 | Kintz et al. |
| 6,069,608 A | 5/2000 | Izumi et al. |
| 6,120,461 A | 9/2000 | Smyth |
| 6,151,061 A | 11/2000 | Tokuhashi |
| 6,351,335 B1 | 2/2002 | Perlin |
| 6,396,461 B1 | 5/2002 | Lewis et al. |
| 6,433,760 B1 | 8/2002 | Vaissie et al. |
| 6,456,262 B1 | 9/2002 | Bell |
| 6,545,650 B1 | 4/2003 | Yamada et al. |
| 6,578,962 B1 | 6/2003 | Amir et al. |
| 6,659,611 B2 | 12/2003 | Amir et al. |
| 6,671,100 B1 | 12/2003 | McRuer |
| 6,864,910 B1 | 3/2005 | Ogino et al. |
| 6,886,137 B2 | 4/2005 | Peck et al. |
| 6,943,754 B2 | 9/2005 | Aughey et al. |
| 7,130,447 B2 | 10/2006 | Aughey et al. |
| 7,193,584 B2 | 3/2007 | Lee |
| 7,193,585 B2 | 3/2007 | Takagi |
| 7,391,887 B2 | 6/2008 | Durnell |
| 7,396,129 B2 | 7/2008 | Endrikhovski et al. |
| 7,401,920 B1 | 7/2008 | Kranz et al. |
| 7,457,434 B2 | 11/2008 | Azar |
| 7,522,344 B1 | 4/2009 | Curatu et al. |
| 7,532,230 B2 | 5/2009 | Culbertson et al. |
| 7,533,988 B2 | 5/2009 | Ebisawa |
| 7,538,744 B1 | 5/2009 | Liu et al. |
| 7,542,210 B2 | 6/2009 | Chirieleison, Sr. |
| 7,618,144 B2 | 11/2009 | Hutchin |
| 7,686,451 B2 | 3/2010 | Cleveland |
| 7,736,000 B2 | 6/2010 | Enriquez et al. |
| 7,809,160 B2 | 10/2010 | Vertegaal et al. |
| 7,883,415 B2 | 2/2011 | Larsen et al. |
| 2002/0105482 A1* | 8/2002 | Lemelson et al. ................. 345/7 |
| 2002/0113755 A1 | 8/2002 | Lee |
| 2002/0163486 A1 | 11/2002 | Ronzani et al. |
| 2002/0167462 A1 | 11/2002 | Lewis et al. |
| 2004/0238732 A1 | 12/2004 | State et al. |
| 2005/0047629 A1 | 3/2005 | Farrell et al. |
| 2005/0190180 A1 | 9/2005 | Jin et al. |
| 2006/0028400 A1 | 2/2006 | Lapstun et al. |
| 2006/0077558 A1 | 4/2006 | Urakawa et al. |
| 2006/0221266 A1 | 10/2006 | Kato et al. |
| 2006/0250322 A1 | 11/2006 | Hall et al. |
| 2007/0132950 A1 | 6/2007 | Victor et al. |
| 2008/0024597 A1 | 1/2008 | Yang et al. |
| 2008/0048931 A1 | 2/2008 | Ben-Ari |
| 2008/0117289 A1 | 5/2008 | Schowengerdt et al. |
| 2008/0181452 A1 | 7/2008 | Kwon et al. |
| 2008/0285140 A1 | 11/2008 | Amitai |
| 2009/0174864 A1 | 7/2009 | Hutchin |
| 2009/0284608 A1 | 11/2009 | Hong et al. |
| 2010/0079356 A1 | 4/2010 | Hoellwarth |
| 2010/0085462 A1 | 4/2010 | Sako et al. |
| 2010/0110368 A1 | 5/2010 | Chaum |
| 2010/0149073 A1 | 6/2010 | Chaum et al. |
| 2010/0289880 A1 | 11/2010 | Moliton et al. |
| 2011/0109880 A1 | 5/2011 | Nummela |
| 2011/0194029 A1 | 8/2011 | Herrmann et al. |
| 2011/0214082 A1* | 9/2011 | Osterhout et al. ............. 715/773 |
| 2012/0021806 A1* | 1/2012 | Maltz ............................. 455/566 |
| 2012/0105486 A1 | 5/2012 | Lankford et al. |
| 2012/0127062 A1 | 5/2012 | Bar-Zeev et al. |
| 2013/0107021 A1 | 5/2013 | Maizels et al. |

FOREIGN PATENT DOCUMENTS

| | | |
|---|---|---|
| EP | 2275856 | 1/2011 |
| JP | 11249588 | 9/1999 |
| JP | 3429320 | 5/2003 |
| JP | 2003520984 | 7/2003 |
| JP | 2009282085 | 12/2009 |
| KR | 20090078085 | 7/2009 |
| WO | 9815868 | 4/1998 |
| WO | 0127685 | 4/2001 |
| WO | WO2009013693 A1 | 1/2009 |

OTHER PUBLICATIONS

Supplemental Notice of Allowance and Fee(s) Due dated Feb. 28, 2013, U.S. Appl. No. 13/221,739, filed Aug. 30, 2011, 6 pages.
U.S. Appl. No. 13/221,739, filed Aug. 30, 2011.
International Search Report and Written Opinion of the International Searching Authority dated Feb. 27, 2013 in International Patent Application No. PCT/US2012/052839, 9 pages.
Lee et al., "Iris Recognition in Wearable Computer", in Zhang et al., Biometric Authentication, First International Conference, ICBA 2004, Jul. 15-17, 2004, vol. 3072 of Lecture Notes in Computer Science, pp. 475-483.
U.S. Appl. No. 13/844,453, filed Mar. 15, 2013.
U.S. Appl. No. 13/689,542, filed Nov. 29, 2012.
Response to Office Action filed Aug. 1, 2013 in U.S. Appl. No. 13/245,700, 10 pages.
International Search Report and Written Opinion dated Mar. 7, 2013 in International Patent Application No. PCT/US2012/057035, 9 pages.
Office Action dated May 1, 2013 in U.S. Appl. No. 13/221,707, 26 pages.
Office Action dated Apr. 25, 2013 in U.S. Appl. No. 13/221,662, 31 pages.
English Abstract for KR20090078085 published Jul. 17, 2009.
International Search Report and Written Opinion of the International Searching Authority dated Feb. 26, 2013 in International Patent Application No. PCT/US2012/052806, 11 pages.
Response to Office Action filed Aug. 26, 2013 in U.S. Appl. No. 13/221,662, 14 pages.
Response to Office Action filed Sep. 3, 2013 in U.S. Appl. No. 13/221,707, 11 pages.
Office Action date Oct. 10, 2013 in U.S. Appl. No. 13/221,770, 41 pages.
Final Office Action dated Oct. 2, 2013 in U.S. Appl. No. 13/245,700, 29 pages.
Final Office Action dated Oct. 1, 2013 in U.S. Appl. No. 13/221,707, 16 pages.
Final Office Action dated Oct. 3, 2013 in U.S. Appl. No. 13/221,662, 24 pages.
Chen et al., "Research on Eye-gaze Tracking Network Generated by Augmented Reality Application", Proceedings of the Second International Workshop on Knowledge Discovery and Data Mining, Jan. 23-25, 2009, pp. 594-597 IEEE, Moscow, Russia, 4 pages.
"Helmet Mounted Display (HMD) with Built-In Eye Tracker", Datasheet, National Aerospace Laboratory (NLR), Jan. 2009, Retrieved from the Internet: URL: <http://www.nlr.nl/ATTS/flyer%20HMD%20F294-03.pdf>, 4 pages.

(56) References Cited

OTHER PUBLICATIONS

Hillaire, et al., "Using an Eye-Tracking System to Improve Camera Motions and Depth-of-Field Blur Effects in Virtual Environments", Proceedings of the 2008 Virtual Reality Conference, Mar. 8-12, 2008, pp. 47-50, IEEE: Reno, NE, USA. Retrieved from the Internet Nov. 11, 2010, URL: <http://www.irisa.fr/bunraku/GENS/alecuyer/vr08_hillaire.pdf>, 4 pages.

Kim et al., "Vision-Based Eye-Gaze Tracking for Human Computer Interface", Proceedings of the 1999 Conference on Systems, Man, and Cybernetics, Oct. 12-15, 1999, pp. 324-329, vol. 2. IEEE: Toyko, Japan, 3 pages.

Lee et al., "Robust Gaze Tracking Method for Stereoscopic Virtual Reality Systems", J. Jacko (Ed.). Proceedings of the 12th international conference on Human-computer interaction: intelligent multimodal interaction environments (HCI'07), Jul. 22-27, 2007, pp. 700-709. Retrieved from the Internet: URL: <http://delivery.acm.org/10.1145/1770000/1769669/p700-lee.pdf?key1=1769669&key2=3272740821&coll=GUIDE&dl=GUIDE&CFID=98778950&CFTOKEN=13851951>, 10 pages.

Liu, et al.,"Real Time Auto-Focus Algorithm for Eye Gaze Tracking System", Proceedings of the 2007 International.Symposium on Intelligent Signal Processing and Communication Systems, Nov. 28-Dec. 1, 2007, pp. 742-745, Xiamen, China, 4 pages.

Rolland, et al., "Displays—Head-Mounted", In Encyclopedia of Optical Engineering, New York: Marcel Dekker, 2005 [retrieved on Nov. 11, 2010] Retrieved from the Internet: URL: <http://www.optics.arizona.edu/opti588/reading/HMD_Rolland_Hua_2005.pdf>, 16 pages.

Nilsson, et al., "Hands Free Interaction with Virtual Information in a Real Environment: Eye Gaze as an Interaction Tool in an Augmented Reality System", PsychNology Journal, vol. 7, No. 2, pp. 175-196, Apr. 28, 2009, 22 pages.

Handa, et al., "Development of head-mounted display with eye-gaze detection function for the severely disabled", 2008 IEEE International Conference on Virtual Environments, Human-Computer Interfaces, and Measurement Systems (VECIMS 2008), Jul. 14-16, 2008, Istanbul, Turkey, 5 pages.

"Head Fixed Eye Tracking System Specifications", Arrington Research [online], Retrieved from the Internet on Jun. 10, 2011: <URL: http://www.arringtonresearch.com/techinfo.html>, 2 pages.

Gang, Wen, "Chapter 3 Gaze Estimation System", National University of Singapore, ScholarBank@NUS[online], 2004 [retrieved on Jun. 10, 2011], Retrieved from the Internet: URL:<http://scholarbank.nus.edu.sg/bitstream/handle/10635/13692/Chapter3_GazeDetectionSystem.pdf?sequence=5>,10 pages.

Reale, et al., "Viewing Direction Estimation Based on 3D Eyeball Construction for HRI", IEEE Computer Society Conference on Computer Vision and Pattern Recognition Workshops, Jun. 13-18, 2010, pp. 24-31, San Francisco, CA, IEEE Publishers, 8 pages.

Ebisawa, Yoshinobu, "Unconstrained Pupil Detection Technique Using Two Light Sources and the Image Difference Method", Visualization and Intelligent Design in Engineering and Architecture II, Published 1995, 11 pages.

Hennessey, et al., "A Single Camera Eye-Gaze Tracking System with Free Head Motion", Proceedings of the 2006 Symposium on Eye Tracking Research and Applications, Mar. 27-29, 2006, pp. 87-94, ACM, New York, NY, 8 pages.

Villanueva, et al., "Geometry Issues of Gaze Estimation", Advances in Human Computer Interaction, Oct. 2008, InTech, pp. 513-534, 22 pages.

Pomplun, et al., "Using Pupil Size as a Measure of Cognition Workload in Video-Based Eye-Tracking Studies", Department of Computer Science, Research Article [online], [retrieved on Jun. 10, 2011] Retrieved from the Internet: <URL: http://www.cs.umb.edu/~marc/pubs/pomplun_sunkara_fairley_xiao_draft.pdf>, 37 pages.

Ajanki, et al., "Ubiquitous Contextual Information Access with Proactive Retrieval and Augmentation", Proceedings of the Fourth International Workshop in Ubiquitous Augmented Reality (IWUVR 2010), May 17, 2010, Helsinki, Finland, 5 pages.

Herbelin, et al., "Coding gaze tracking data with chromatic gradients for VR Exposure Therapy", Proceedings of the 17th International Conference on Artificial Reality and Telexistence (ICAT '07), Nov. 28-30, 2007, Esbjerg, Denmark, 8 pages.

Kollenberg, et al., "Visual Search in the (Un)Real World: How Head-Mounted Displays Affect Eye Movements, Head Movements and Target Detection", Proceedings of the 2010 Symposium on Eye-Tracking Research & Applications (ETRA '10), Mar. 22-24, 2010, Austin Texas, 4 pages.

ZionEyez, A Social Media Company [online], Copyright ZionEyez 2011 [retrieved on Jun. 15, 2011], Retrieved from the Internet: <URL:http://www.zioneyez.com/#/home/>, 6 pages.

Canadian Office Action dated Nov. 7, 2011, Canadian Patent Application No. 2,750,287 filed Aug. 29, 2011, 3 pages.

Response to Canadian Office Action dated Jan. 31, 2012, Canadian Patent Application No. 2,750,287 filed Aug. 29, 2011, 12 pages.

Canadian Office Action dated Feb. 22, 2012, Canadian Patent Application No. 2,750,287 filed Aug. 29, 2011, 1 page.

Response to Canadian Office Action dated Feb. 28, 2012, Canadian Patent Application No. 2,750,287 filed Aug. 29, 2011, 75 pages.

Ajanki, et al. "Contextual Information Access with Augmented Reality." in Proceedings of IEEE International Workshop on Machine Learning for Signal Processing (MLSP), Aug. 29-Sep. 1, 2010, pp. 95-100: Kittila, Finland, 6 pages.

Li, et al., "An Efficient Method for Eye Tracking and Eye-Gazed FOV Estimation," Proceedings of the 16th IEEE international conference on Image processing (ICIP'09), pp. 2597-2600, Nov. 2009, Cairo, Egypt, 4 pages.

Lin et al., "A new data processing and calibration method for an eye-tracking device pronunciation system," Optics & Laser Technology, Apr. 2002, vol. 34, pp. 405-413. Elsevier Science Ltd. New York, NY, USA, 9 pages.

"Technology: PicoP Display Engine—How it Works," MicroVision: PicoP Technology [online], Retrieved from the Internet [retrieved on Sep. 21, 2011], <URL: http://www.microvision.com/technology/picop.html>, 46 pages.

U.S. Appl. No. 13/245,700, filed Sep. 26, 2011.
U.S. Appl. No. 13/221,707, filed Aug. 30, 2011.
U.S. Appl. No. 13/221,669, filed Aug. 30, 2011.
U.S. Appl. No. 13/221,662, filed Aug. 30, 2011.
U.S. Appl. No. 13/221,770, filed Aug. 30, 2011.

Office Action dated Sep. 14, 2012, U.S. Appl. No. 13/221,707, filed Aug. 30, 2011, 35 pages.

Office Action dated Sep. 13, 2012, U.S. Appl. No. 13/221,662, filed Aug. 30, 2011, 37 pages.

Ji, et al., "Eye and Gaze Tracking for Interactive Graphic Display", In Journal of Machine Vision and Applications, vol. 15, Issue 3, Jun. 8, 2004, 10 pages.

Akeley et al., "A Stereo Display Prototype with Multiple Focal Distances", Proceedings of ACM SIGGRAPH, Aug. 2004, pp. 804-813. ACM, Inc., New York, NY, USA, 10 pages.

Blum, et al., "The Effect of Out-of-focus Blur on Visual Discomfort When Using Stereo Displays", Proceedings of the 2010 International Symposium on Mixed and Augmented Reality, Oct. 13-16, 2010, pp. 13-17, IEEE: Seoul, Korea, 5 pages.

Barras, Colin, "Innovation: Gaze trackers eye computer gamers", NewScientist [online]. Mar. 26, 2010 [retrieved.On Aug. 26, 2010] Retrieved from the Internet: URL: <http://www.newscientist.com/article/dn18707-innovation-gaze-trackers-e>, 4 pages.

"Gaze-enhanced User Interface Design", Stanford HCI Group [online]. Retrieved from the Internet on Aug. 27, 2010: URL: <http://hci.stanford.edu/research/GUIDe/>, 3 pages.

Cadden, Ricky, "Nokia Has Been Fine-Tuning Eye-Tracking Glasses", Symbian-Guru.com [online], Sep. 6, 2009 [retrieved on Aug. 26, 2010] Retrieved from the Internet: URL: <http://www.symbian-guru.com/welcome/2009/09/nokia-has-been-fine-tuning-eye-tracking-glasses.html>, 3 pages.

Livingston et al., "Vertical Vergence Calibration for Augmented Reality Displays", Proceedings of the IEEE Conference on Virtual Reality, pp. 293-294, Mar. 25-29, 2006, Alexandria, Virginia, USA, 2 pages.

(56) References Cited

OTHER PUBLICATIONS

Owen, et al, "Display-Relative Calibration for Optical See-Through Head-Mounted Displays", Proceedings of the Third IEEE and ACM International Symposium on Mixed and Augmented Reality (ISMAR 2004), Nov. 2-5, 2004, Arlington, Virginia, USA, 9 pages.

Pansing, et al., "Optimization of illumination schemes in a head-mounted display integrated with eye tracking capabilities", Proceedings of the SPIE International Society for Optical Engineering, vol. 5875, Aug. 2005, San Diego, California, USA, 13 pages.

Hua, et al., "Modeling of an eye-imaging system for optimizing illumination schemes in an eye-tracked head-mounted display," Applied Optics, Nov. 2007, vol. 46, No. 31, Optical Society of America: Washington, DC, USA, 14 pages.

Response to Office Action filed Jan. 14, 2013, U.S. Appl. No. 13/227,707, filed Aug. 30, 2011, 9 pages.

Response to Office Action filed Jan. 14, 2013, U.S. Appl. No. 13/221,662, filed Aug. 30, 2011, 11 pages.

Office Action dated Feb. 1, 2013, U.S. Appl. No. 13/245,700, filed Sep. 26, 2011, 35 pages.

Office Action dated Sep. 6, 2012, U.S. Appl. No. 13/221,739 filed Aug. 30, 2011, 61 pages.

Response to Office Action filed Oct. 16, 2012, U.S. Appl. No. 13/221,739, filed Aug. 30, 2011, 12 pages.

Response to Office Action filed Jan. 10, 2014, in U.S. Appl. No. 13/221,770.

Response to Office Action filed Feb. 3, 2014, in U.S. Appl. No. 13/221,707.

Response to Final Office Action filed Mar. 3, 2013, in U.S. Appl. No. 13/221,662.

Office Action dated May 5, 2014 in Chinese Patent Application No. 201210362802.8, with English summary, 15 pages.

English Abstract of PCT Publication No. WO2009013693A1 published Jan. 29, 2009, 1 page.

Machine translation of Chinese Publication No. CN1771454A, published May 10, 2006, 10 pages.

Final Office Action dated Apr. 18, 2014 in U.S. Appl. No. 13/221,770, 22 pages.

Response to Office Action filed Apr. 2, 2014 in U.S. Appl. No. 13/245,700, 10 pages.

Office Action dated May 13, 2014 in U.S. Appl. No. 13/245,700, 15 pages.

Office Action dated Jun. 5, 2014 in U.S. Appl. No. 13/221,707, 17 pages.

Office Action dated Jun. 6, 2014 in U.S. Appl. No. 13/221,662, 25 pages.

Notice of Allowance dated Nov. 19, 2014, in U.S. Appl. No. 13/844,453, filed Mar. 15, 2013.

\* cited by examiner

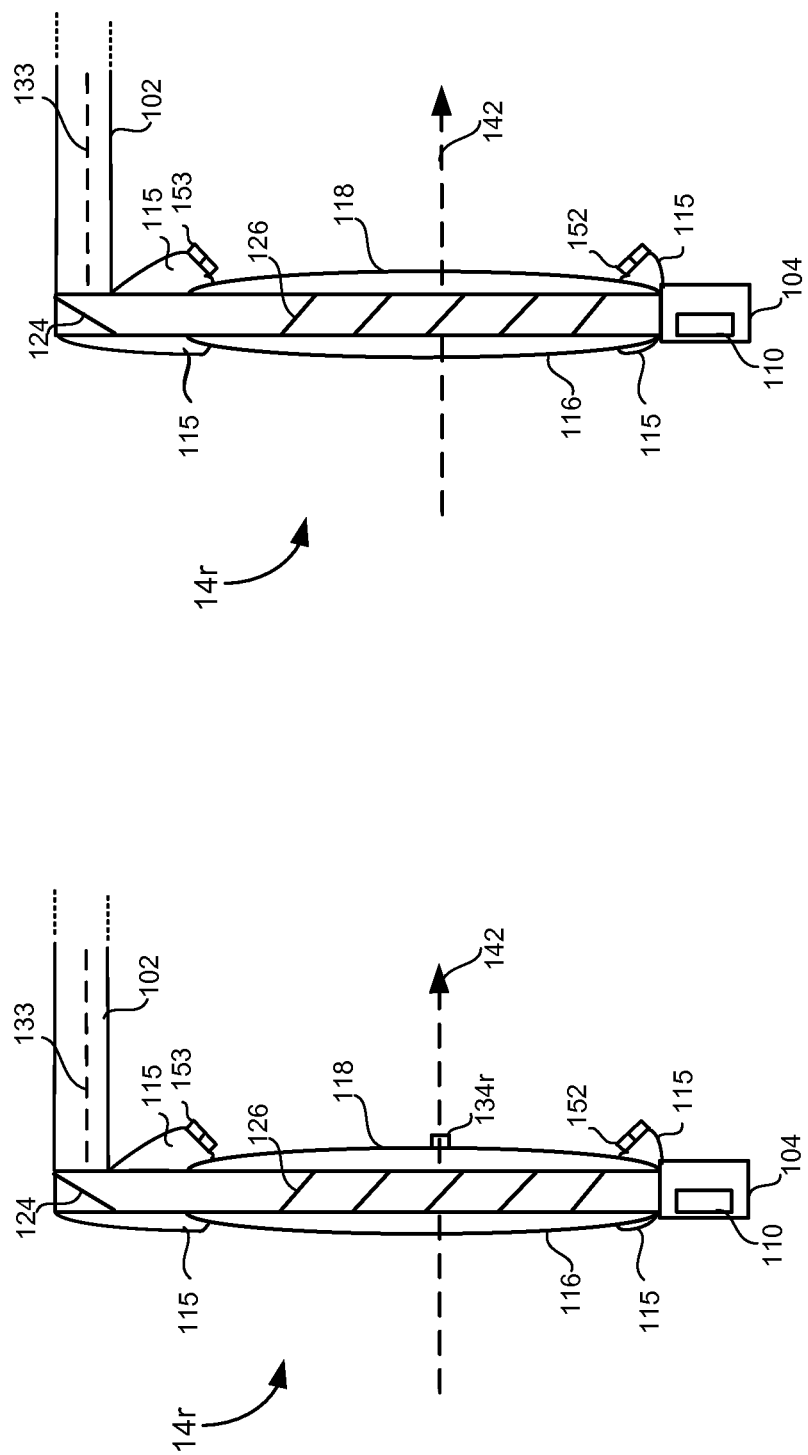

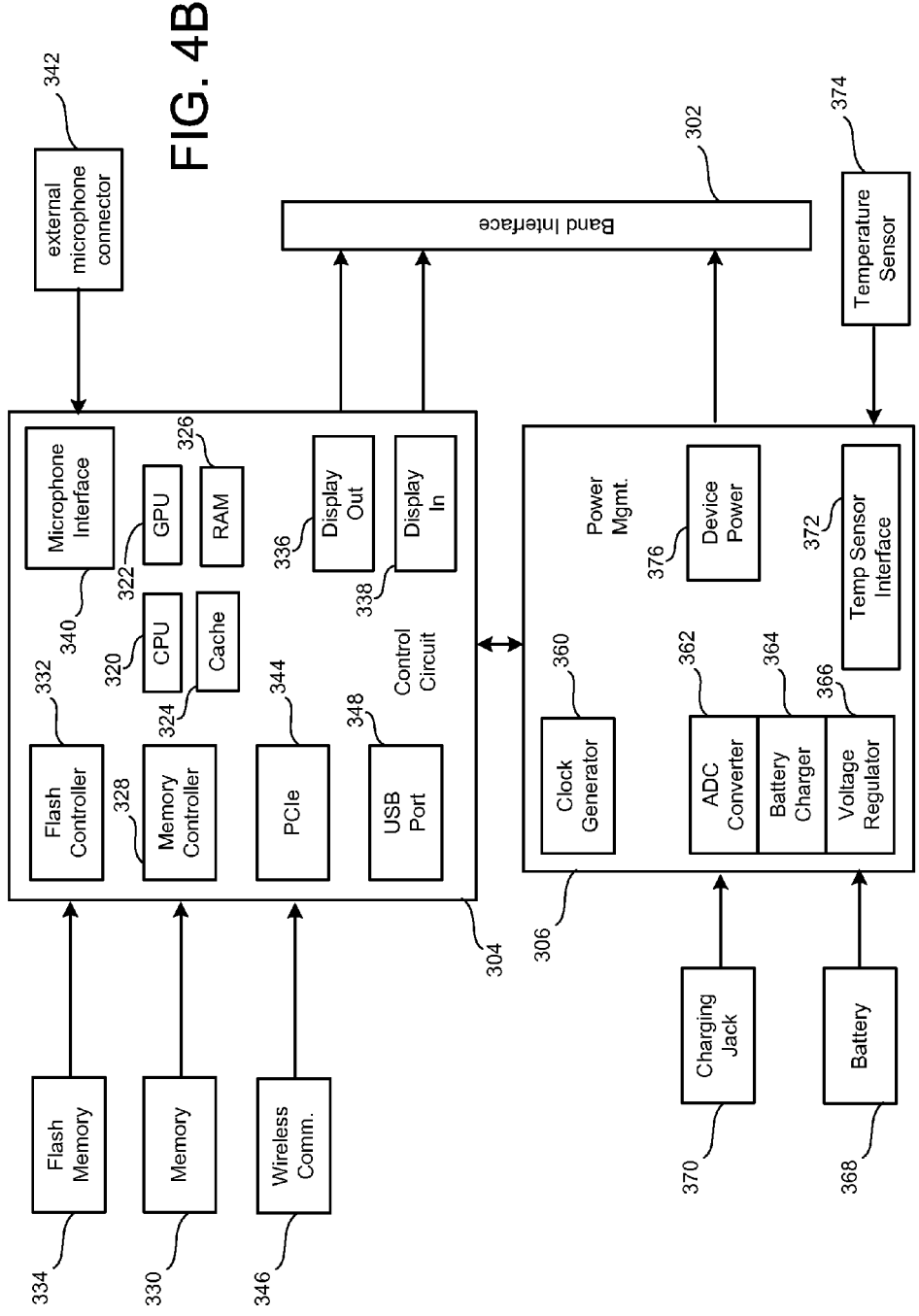

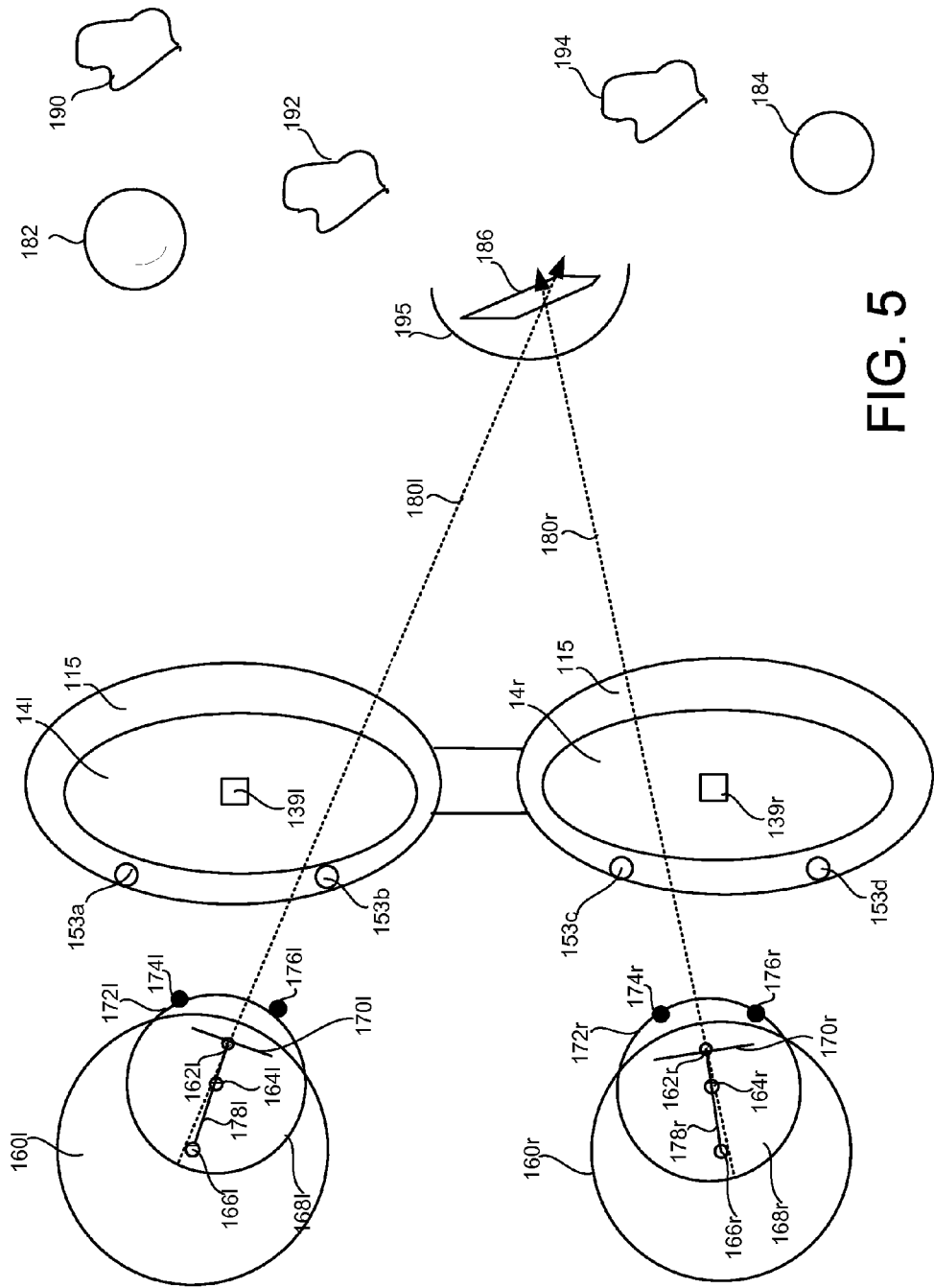

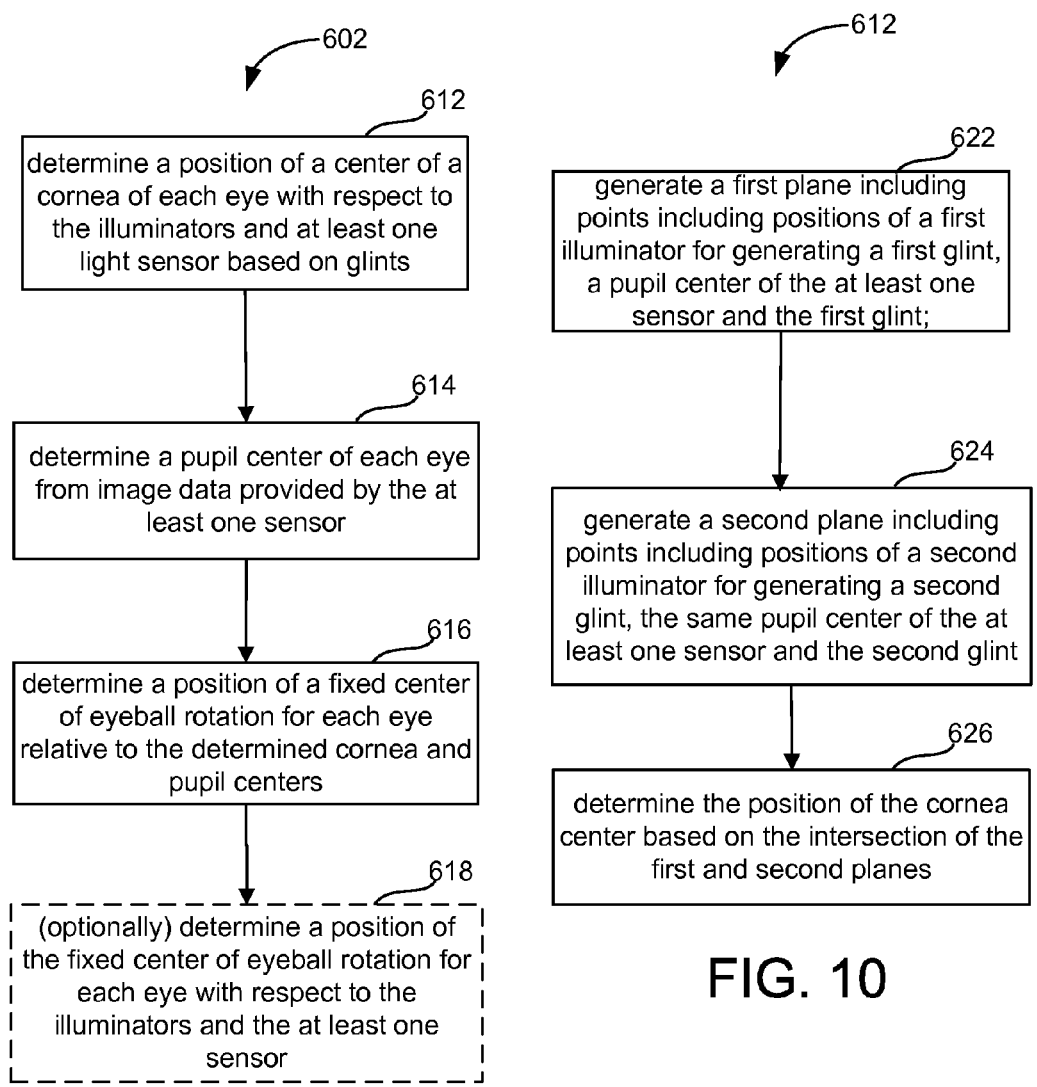

GAZE DETECTION IN A SEE-THROUGH, NEAR-EYE, MIXED REALITY DISPLAY

CROSS-REFERENCE TO RELATED APPLICATION

This application is a continuation of and claims priority from U.S. patent application Ser. No. 13/221,739 to Lewis et al. entitled "Gaze Detection in a See-Through, Near-Eye, Mixed Reality Display" which was filed Aug. 30, 2011 which also claims the benefit of priority from Canadian Application No. 2,750,287 to Lewis et al. of the same title and which was filed Aug. 29, 2011, and U.S. patent application Ser. No. 13/844,453 to Lewis et al. entitled "Gaze Detection in a See-Through, Near-Eye, Mixed Reality Display" which was filed Mar. 15, 2013, which parent applications are hereby incorporated by reference.

BACKGROUND

Augmented or mixed reality is a technology that allows virtual imagery to be mixed with a user's actual view of the real world. A near-eye display may be worn by a user to view the mixed imagery of virtual and real objects. A near-eye display displays virtual imagery in the user's field of view. However, the user's field of view is not stationary as a user moves his or her head. Furthermore, what the user is looking at in the field of view changes as the user shifts his or her eyes, even if his or her head does not move.

SUMMARY

The technology provides various embodiments for gaze determination within a see-through, near-eye mixed reality display device. Gaze is sometimes referred to as a line of sight from the user's eye to an object, real or virtual, at which the user is looking. Embodiments are provided for determining gaze based on glint data or a combination of both glint and image data. In some embodiments, a gaze determination coordinate system based on predetermined positioning of at least one light sensor and illuminators on the display device provides a three dimensional (3D) spatial relationship between the display device and each respective eye. A gaze vector for each eye may be determined based on the 3D spatial relationship. Based on gaze vectors for both eyes, a point of gaze may be determined which indicates one or more objects, real or virtual, at which a user is gazing, or more commonly stated as, at which the user is looking.

The technology provides an embodiment of a mixed reality display system with gaze determination. The system embodiment comprises a see-through, near-eye display device including a respective display optical system for each eye positioned to be seen through by the respective eye. For each eye, an image generation unit is attached to the see-through display device for generating at least one virtual image for display. Additionally, the embodiment includes a respective arrangement of gaze detection elements positioned on the display device for forming a spatial relationship between the gaze detection elements and each eye. The gaze detection elements include a set of illuminators for generating glints on the respective eye, and at least one respective sensor for capturing light reflected from the respective eye and generating data representing the captured reflected light. The system embodiment includes memory for storing software and the data. A processor is communicatively coupled to the at least one respective sensor for receiving and storing the data representing the captured reflected light in the accessible memory. The processor determines a gaze vector for each respective eye based on the data representing the captured reflected light and a point of gaze based on the gaze vectors in a three-dimensional (3D) user field of view.

The technology provides an embodiment of a method for determining gaze in a see-through, near-eye mixed reality display system. The method embodiment comprising determining boundaries of a gaze detection coordinate system based on positions of glints detected on a user eye, positions on the near-eye display system of illuminators for generating the glints; and a position of at least one sensor for detecting the glints. The method further comprises determining a gaze vector for each eye based on reflected eye data including the glints; determining a point of gaze based on the gaze vectors for the two eyes in a three-dimensional (3D) user field of view including real and virtual objects, and identifying any object at the point of gaze in the 3D user field of view.

Another system embodiment is also provided by the technology for a mixed reality display system with gaze determination based on glints. The system comprises a see-through, near-eye display device including a respective display optical system for each eye positioned to be seen through by the respective eye and a respective image generation unit for each eye attached to the see-through display device for generating at least one virtual image for display. The system further comprises a set of infra-red (IR) illuminators for producing glints for each eye and at least one respective sensor is positioned on the near-eye display device at a predetermined position to detect the glints and generate glint data to be stored in a memory accessible by a processor which determines a gaze vector for each eye based on the glint data. A point of gaze in a three-dimensional user field of view is determined by the software controlled processor based on the gaze vectors.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 3C is a top view of a third embodiment of a display optical system of a see-through, near-eye, mixed reality device including an arrangement of gaze detection elements in a gaze detection system.

FIG. 3D is a top view of a fourth embodiment of a display optical system of a see-through, near-eye, mixed reality device including an arrangement of gaze detection elements in a gaze detection system.

FIG. 4B is a block diagram of one embodiment of the hardware and software components of a processing unit associated with a see-through, near-eye, mixed reality display unit.

FIG. 5 is a top view illustrating examples of gaze vectors intersecting at a point of gaze where a user's eyes are focused.

FIG. 9 is a flowchart of a method embodiment which may be used to determine boundaries for a gaze detection coordinate system.

FIG. 10 is a flowchart illustrating a method embodiment for determining a position of a center of a cornea in the coordinate system with optical gaze detection elements of the see-through, near-eye, mixed reality display.

DETAILED DESCRIPTION

Figure 1A:
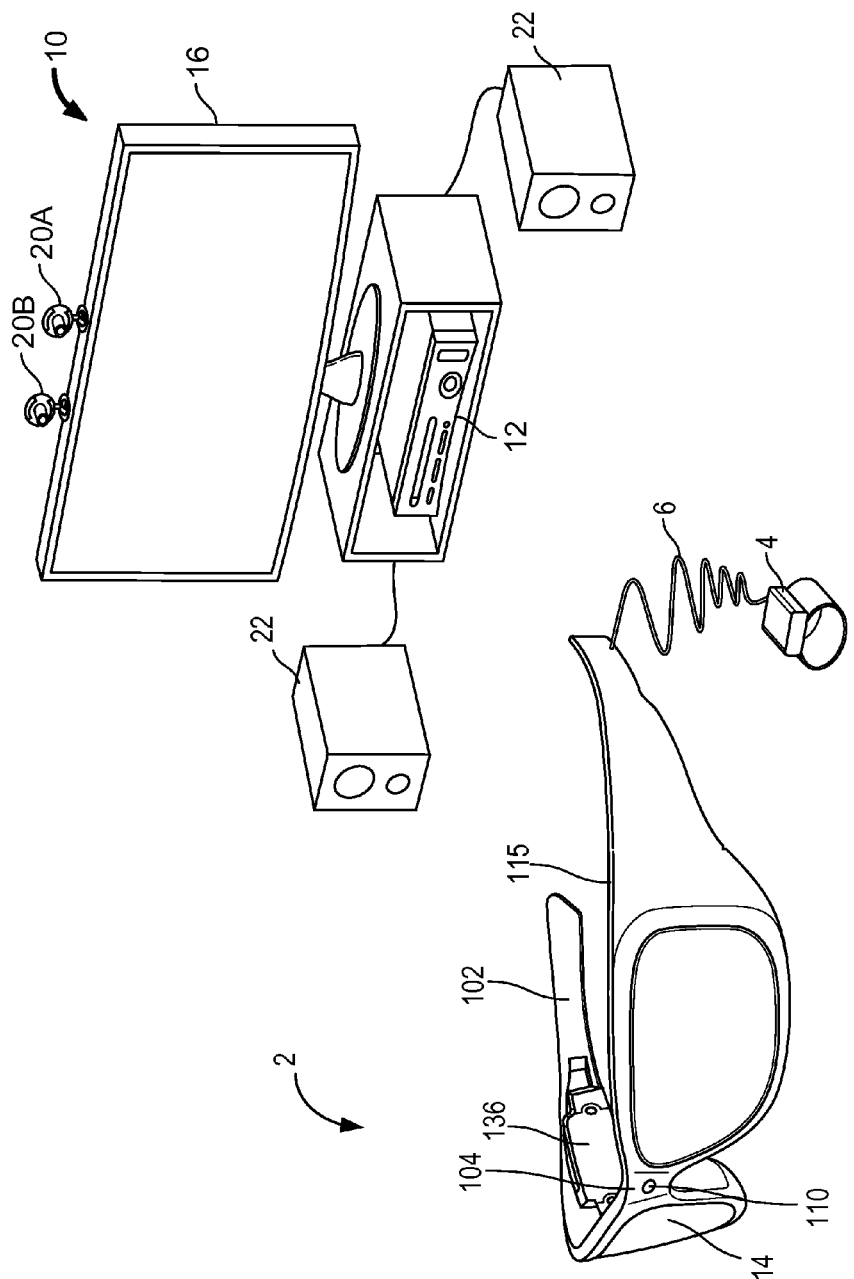
FIG. 1A is a block diagram depicting example components of one embodiment of a see-through, mixed reality display device with gaze determination.

The technology provides various embodiments for gaze determination within a see-through, near-eye, mixed reality display device. Gaze is sometimes referred to as a line of sight or a visual axis of an eye. The visual axis extends from the fovea, sometimes referred to as the foveal centralis, of the retina through the center of the pupil. Extending the visual axis from the fovea through the pupil and a see-through lens for each eye, one can determine a point of gaze in a user's field of view which may include images of virtual objects, and an actual direct view of the real world.

The use of the term "actual direct view" refers to the ability to see real world objects directly with the human eye, rather than seeing created image representations of the objects. For example, looking through glass at a room allows a user to have an actual direct view of the room, while viewing a video of a room on a television is not an actual direct view of the room. Based on the context of executing software, for example, a gaming application, the system can project images of virtual objects, sometimes referred to as virtual images, on the display that are viewable by the person wearing the see-through display device while that person is also viewing real world objects through the display.

Geometry of one or more gaze detection elements with respect to the visible portion of a human eye forms a basis for various embodiments of gaze determination. In some embodiments, data from only glints may be used to track changing intensities due to different reflectivities on parts of the eye like the sclera, sometimes referred to as the white section of the eye, the pupil and the iris. A glint is a very small and often very bright reflection of light from a light source off of a surface of the cornea of an eye. The glint is an image of the light source, typically a narrow beam source focused on the eye. In some embodiments, a training or calibration gaze data set for the glints may be used in comparisons for detecting a current gaze.

Other embodiments use both image data of the eye and data representing glints in the context of a geometry of the illuminators and at least one image sensor to determine boundaries of a three-dimensional (3D) spatial relationship between positions of parts of the eye and a respective system of gaze detection elements. Examples of such parts of the eye are a center of a cornea determined based on glint data, a center of a pupil determined from image data of an eye, and a center of rotation of the eye a position of which is estimated based on the position of the cornea center. For accuracy considerations in gaze determination purposes, the center of rotation of the eyeball may be considered fixed. A gaze vector for the respective eye is determined based on the cornea center, pupil center, and center of rotation which form an optical axis for the respective eye. An angle offset may be applied to the optical axis in order to obtain a visual axis for the eye which may be selected as the gaze vector.

Different gaze detection techniques may be used within the same system. For example, due to obstructions of the eye or update processing time, less computationally intensive techniques, like a version of the approach based on correlating glint intensity values with pupil position, may be used more frequently in combination with more computationally intensive techniques run with longer time intervals in between like a version of determining the gaze vector based on the 3D spatial relationship between the cornea center, pupil center, center of rotation and a gaze detection system of optical elements. Changes in the spatial relationship including depth changes between the eye and the gaze detection elements can be determined also as an indicator triggering recalibration of the system, for example in embodiments using a training gaze data set.

In the embodiments discussed below, the see-through display device is in a set of eyeglasses but other head mounted display (HMD) formats and near-eye display holders suitable for consumer, everyday use can be used as well.

FIG. 1A is a block diagram depicting example components of one embodiment of a mixed reality display system with gaze determination. System 10 includes a see-through display device as a near-eye, head mounted display device 2 in communication with processing unit 4 via wire 6. In other embodiments, head mounted display device 2 communicates with processing unit 4 via wireless communication. Processing unit 4 may take various embodiments. In some embodiments, processing unit 4 is a separate unit which may be worn on the user's body, e.g. the wrist in the illustrated example or in a pocket, and includes much of the computing power used to operate near-eye display device 2. Processing unit 4 may communicate wirelessly (e.g., WiFi, Bluetooth, infra-red, or other wireless communication means) to one or more hub computing systems 12. In other embodiments, the functionality of the processing unit 4 may be integrated in software and hardware components of the display device 2.

Head mounted display device 2, which in one embodiment is in the shape of eyeglasses in a frame 115, is worn on the head of a user so that the user can see through a display, embodied in this example as a display optical system 14 for each eye, and thereby have an actual direct view of the space in front of the user. Frame 115 provides a support for holding elements of the system in place as well as a conduit for electrical connections. In this embodiment, frame 115 provides a convenient eyeglass frame as support for the elements of the system discussed further below. In other embodiments, other support structures can be used. An example of such a structure is a visor or goggles. The frame 115 includes a temple or side arm for resting on each of a user's ears. Temple 102 is representative of an embodiment of the right temple. Nose bridge 104 of the frame includes a microphone 110 for recording sounds and transmitting audio data to processing unit 4.

Hub computing system 12 may be a computer, a gaming system or console, or the like. According to an example embodiment, the hub computing system 12 may include hardware components and/or software components such that hub computing system 12 may be used to execute applications such as gaming applications, non-gaming applications, or the like. In one embodiment, hub computing system 12 may include a processor such as a standardized processor, a specialized processor, a microprocessor, or the like that may execute instructions stored on a processor readable storage device for performing the processes described herein.

Hub computing system 12 further includes one or more capture devices, such as capture devices 20A and 20B. In other embodiments, more or less than two capture devices can be used to capture the room or other physical environment of the user. Capture devices 20A and 20B may be, for example, cameras that visually monitor one or more users and the surrounding space such that gestures and/or movements performed by the one or more users, as well as the structure of the surrounding space, may be captured, analyzed, and tracked to perform one or more controls or actions within an application and/or animate an avatar or on-screen character. An application may be executing on hub computing system 12, the display device 2, as discussed below on a mobile device 5 or a combination of these.

Hub computing system 12 may be connected to an audiovisual device 16 such as a television, a monitor, a high-definition television (HDTV), or the like that may provide game or application visuals. In some instances, the audiovisual device 16 may be a three-dimensional display device. For example, hub computing system 12 may include a video adapter such as a graphics card and/or an audio adapter such as a sound card that may provide audiovisual signals associated with the game application, non-game application, etc. The audiovisual device 16 may receive the audiovisual signals from hub computing system 12 and may then output the game or application visuals and/or audio associated with the audiovisual signals. According to one embodiment, the audiovisual device 16 may be connected to hub computing system 12 via, for example, an S-Video cable, a coaxial cable, an HDMI cable, a DVI cable, a VGA cable, component video cable, RCA cables, etc. In one example, audiovisual device 16 includes internal speakers. In other embodiments, audiovisual device 16, a separate stereo or hub computing system 12 is connected to external speakers 22.

Figure 1B:
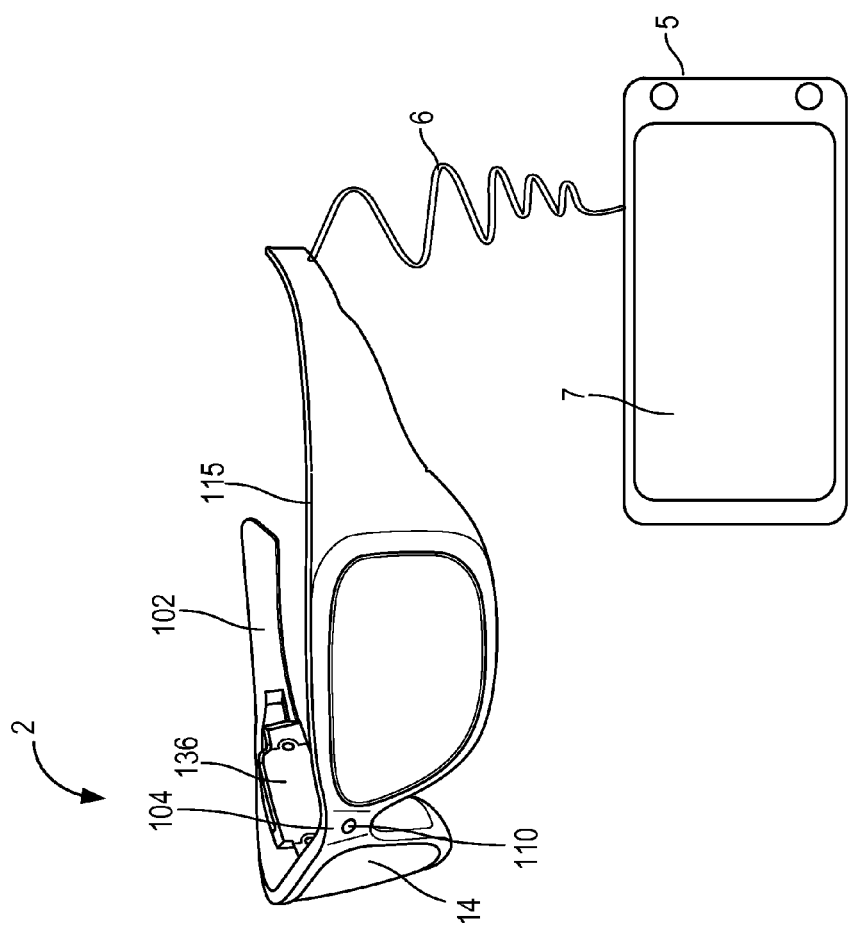
FIG. 1B is a block diagram depicting example components of another embodiment of a see-through, mixed reality display device with gaze determination.

FIG. 1B is a block diagram depicting example components of another embodiment of a mixed reality display system with gaze determination. In this embodiment, the near-eye display device 2 communicates with a mobile computing device 5 as an example embodiment of the processing unit 4. In the illustrated example, the mobile device 5 communicates via wire 6, but communication may also be wireless in other examples.

Furthermore, as in the hub computing system 12, gaming and non-gaming applications may execute on a processor of the mobile device 5 which user actions control or which user actions animate an avatar as may be displayed on a display 7 of the device 5. The mobile device 5 also provides a network interface for communicating with other computing devices like hub computing system 12 over the Internet or another communication network via a wired or wireless communication medium using a wired or wireless communication protocol. A remote network accessible computer system like hub computing system 12 may be leveraged for processing power and remote data access by a processing unit 4 like mobile device 5. Examples of hardware and software components of a mobile device 5 such as may be embodied in a smartphone or tablet computing device are described in FIG. 16, and these components can embody the hardware and software components of a processing unit 4 such as those discussed in the embodiment of FIG. 4A. Some other examples of mobile devices 5 are a laptop or notebook computer and a netbook computer.

As noted above, in some embodiments, gaze detection of each of a user's eyes is based on a three dimensional coordinate system of gaze detection elements on a near-eye, mixed reality display device like the eyeglasses 2 in relation to one or more human eye elements such as a cornea center, a center of eyeball rotation and a pupil center. Examples of gaze detection elements which may be part of the coordinate system including glint generating illuminators and at least one sensor for capturing data representing the generated glints. As discussed in the embodiment of FIG. 7, a center of the cornea can be determined based on two glints using planar geometry. The center of the cornea links the pupil center and the center of rotation of the eyeball, which may be treated as a fixed location for determining an optical axis of the user's eye at a certain gaze or viewing angle.

Figure 1C:
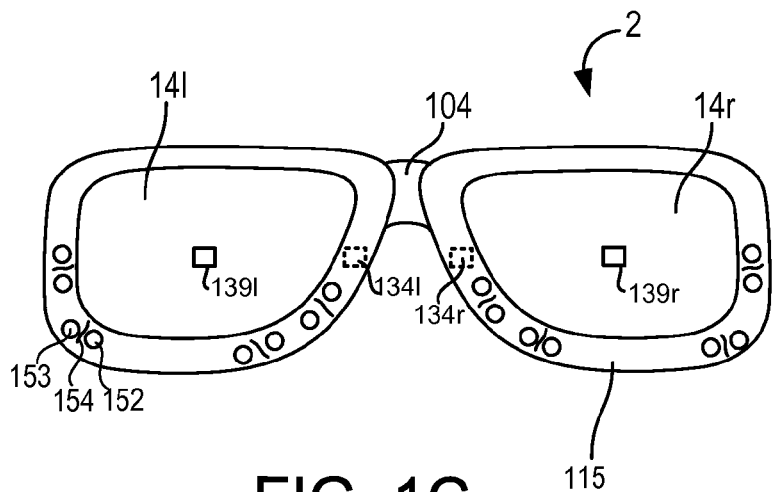
FIG. 1C illustrates an exemplary arrangement of positions of respective sets of gaze detection elements in a gaze detection system for each eye positioned facing each respective eye on a mixed reality display device embodied in a set of eyeglasses.

FIG. 1C illustrates an exemplary arrangement of positions of respective sets of gaze detection elements in a gaze detection system for each eye positioned facing each respective eye by a see-through, near-eye, mixed reality display system embodied in a set of eyeglasses 2. What appears as a lens for each eye represents a display optical system 14 for each eye, e.g. 14r and 14l. A display optical system includes a see-through lens, e.g. 118 and 116 in FIGS. 3A-3D, as in an ordinary pair of glasses, but also contains optical elements (e.g. mirrors, filters) for seamlessly fusing virtual content with the actual and direct real world view seen through the lens 118, 116. A display optical system 14 has an optical axis which is generally in the center of the see-through lens 118, 116 in which light is generally collimated to provide a distortionless view. For example, when an eye care professional fits an ordinary pair of eyeglasses to a user's face, a goal is that the glasses sit on the user's nose at a position where each pupil is aligned with the center or optical axis of the respective lens resulting in generally collimated light reaching the user's eye for a clear or distortionless view.

In the example of FIG. 1C, a detection area 139r, 139l of at least one sensor is aligned with the optical axis of its respective display optical system 14r, 14l so that the center of the detection area 139r, 139l is capturing light along the optical axis. If the display optical system 14 is aligned with the user's pupil, each detection area 139 of the respective sensor 134 is aligned with the user's pupil. Reflected light of the detection area 139 is transferred via one or more optical elements to the actual image sensor 134 of the camera, in this example illustrated by dashed line as being inside the frame 115.

In one example, a visible light camera also commonly referred to as an RGB camera may be the sensor, and an example of an optical element or light directing element is a visible light reflecting mirror which is partially transmissive and partially reflective. The visible light camera provides image data of the pupil of the user's eye, while IR photodetectors 152 capture glints which are reflections in the IR portion of the spectrum. If a visible light camera is used, reflections of virtual images may appear in the eye data captured by the camera. An image filtering technique may be used to remove the virtual image reflections if desired. An IR camera is not sensitive to the virtual image reflections on the eye.

In other examples, the at least one sensor 134 is an IR camera or a position sensitive detector (PSD) to which IR radiation may be directed. For example, a hot reflecting surface may transmit visible light but reflect IR radiation. The IR radiation reflected from the eye may be from incident radiation of the illuminators 153, other IR illuminators (not shown) or from ambient IR radiation reflected off the eye. In some examples, sensor 134 may be a combination of an RGB and an IR camera, and the optical light directing elements may include a visible light reflecting or diverting element and an IR radiation reflecting or diverting element. In some examples, a camera may be small, e.g. 2 millimeters (mm) by 2 mm. An example of such a camera sensor is the Omnivision OV7727. In other examples, the camera may be small enough, e.g. the Omnivision OV7727, e.g. that the image sensor or camera 134 may be centered on the optical axis or other location of the display optical system 14. For example, the camera 134 may be embedded within a lens of the system 14. Additionally, an image filtering technique may be applied to blend the camera into a user field of view to lessen any distraction to the user.

In the example of FIG. 1C, there are four sets of an illuminator 153 paired with a photodetector 152 and separated by a barrier 154 to avoid interference between the incident light generated by the illuminator 153 and the reflected light received at the photodetector 152. To avoid unnecessary clutter in the drawings, drawing numerals are shown with respect to a representative pair. Each illuminator may be an infra-red (IR) illuminator which generates a narrow beam of light at about a predetermined wavelength. Each of the photodetectors may be selected to capture light at about the predetermined wavelength. Infra-red may also include near-infrared. As there can be wavelength drift of an illuminator or photodetector or a small range about a wavelength may be acceptable, the illuminator and photodetector may have a tolerance range about a wavelength for generation and detection. In embodiments where the sensor is an IR camera or IR position sensitive detector (PSD), the photodetectors may be additional data capture devices and may also be used to monitor the operation of the illuminators, e.g. wavelength drift, beam width changes, etc. The photodetectors may also provide glint data with a visible light camera as the sensor 134.

As mentioned above, in some embodiments which calculate a cornea center as part of determining a gaze vector, two glints, and therefore two illuminators will suffice. However, other embodiments may use additional glints in determining a pupil position and hence a gaze vector. As eye data representing the glints is repeatedly captured, for example at 30 frames a second or greater, data for one glint may be blocked by an eyelid or even an eyelash, but data may be gathered by a glint generated by another illuminator.

Figure 1D:
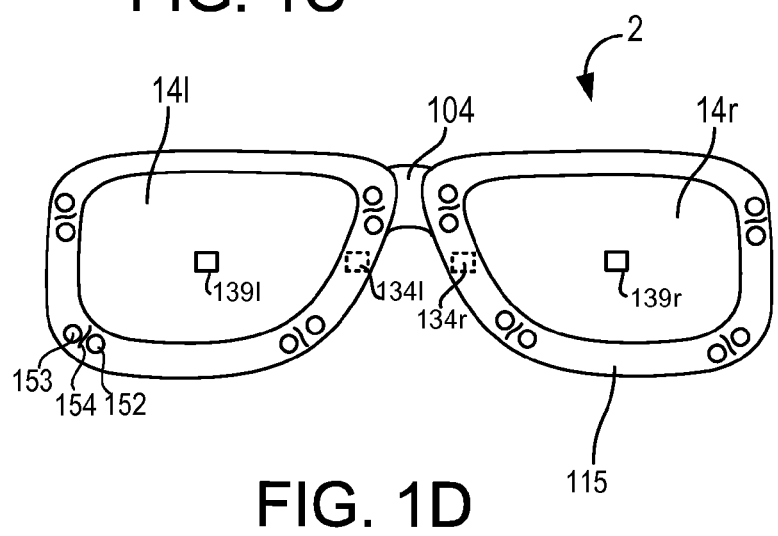
FIG. 1D illustrates another exemplary arrangement of positions of respective sets of gaze detection elements in a gaze detection system for each eye positioned facing each respective eye on a mixed reality display device embodied in a set of eyeglasses.

FIG. 1D illustrates another exemplary arrangement of positions of respective sets of gaze detection elements in a gaze detection system for each eye positioned facing each respective eye on a mixed reality display device embodied in a set of eyeglasses. In this embodiment, two sets of illuminator 153 and photodetector 152 pairs are positioned near the top of each frame portion 115 surrounding a display optical system 14, and another two sets of illuminator and photodetector pairs are positioned near the bottom of each frame portion 115 for illustrating another example of a geometrical relationship between illuminators and hence the glints they generate. This arrangement of glints may provide more information on a pupil position in the vertical direction.

Figure 1E:
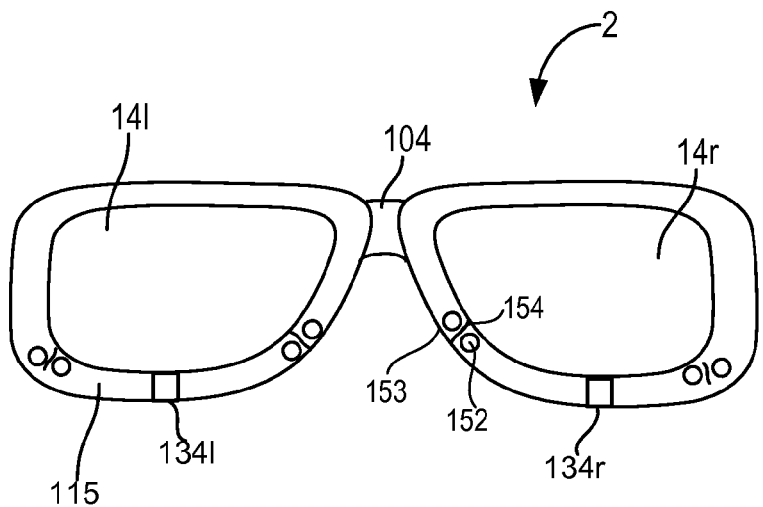
FIG. 1E illustrates yet another exemplary arrangement of positions of respective sets of gaze detection elements in a gaze detection system for each eye positioned facing each respective eye by the set of eyeglasses.

FIG. 1E illustrates yet another exemplary arrangement of positions of respective sets of gaze detection elements in a gaze detection system for each eye positioned facing each respective eye by the set of eyeglasses. In this example, the sensor 134r, 134l is in line or aligned with the optical axis of its respective display optical system 14r, 14l but located on the frame 115 below the system 14. Additionally, in some embodiments, the camera 134 may be a depth camera or include a depth sensor. In this example, there are two sets of illuminators 153 and photodetectors 152.

Figure 2:
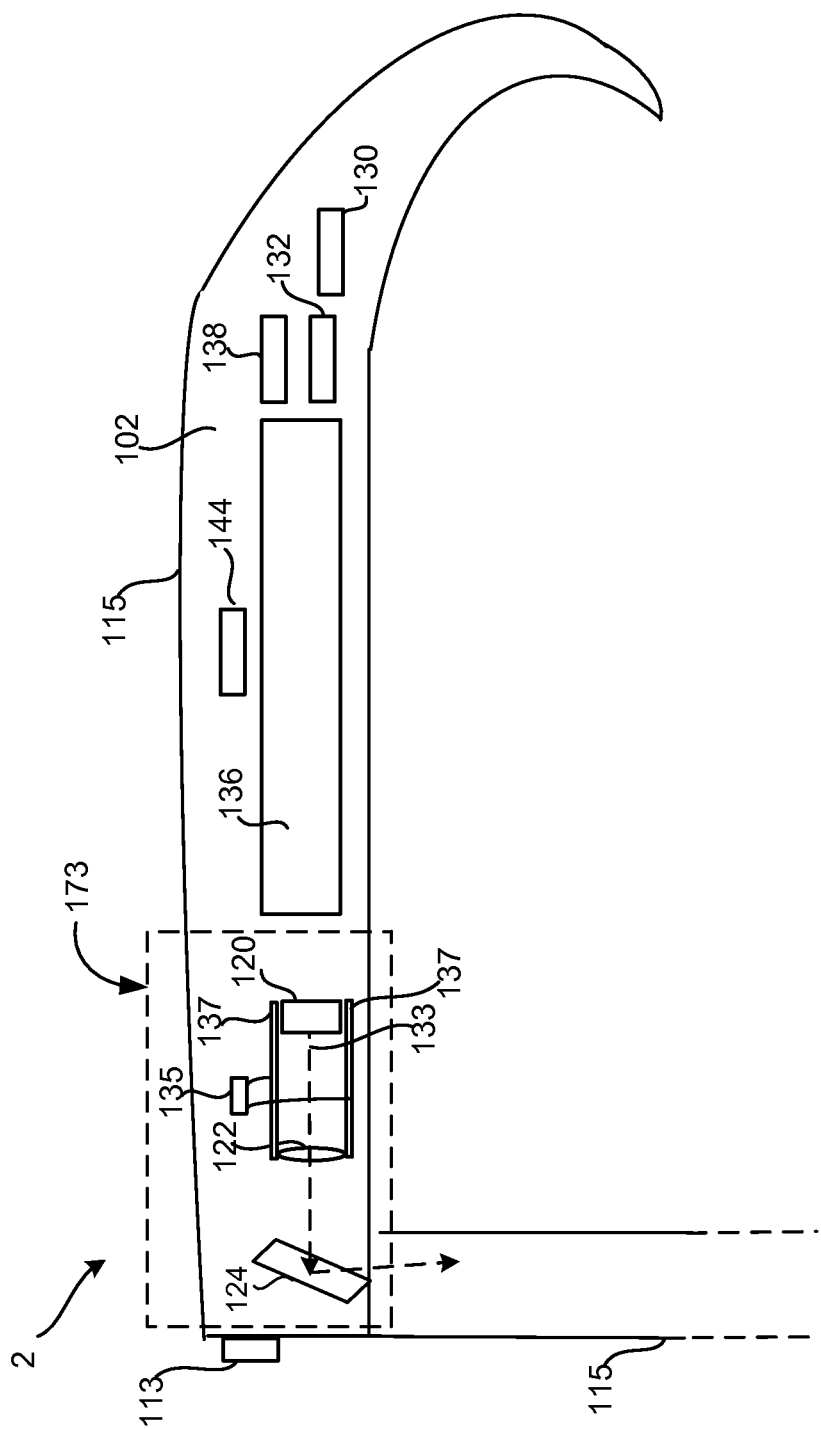
FIG. 2 is a side view of an eyeglass temple in an embodiment of a mixed reality display device providing support for hardware and software components.

FIG. 2 is a side view of an eyeglass temple 102 of the frame 115 in an embodiment of the see-through, mixed reality display device embodied as eyeglasses providing support for hardware and software components. At the front of frame 115 is physical environment facing video camera 113 that can capture video and still images. Particularly in some embodiments where the display device 2 is not operating in conjunction with depth cameras like capture devices 20a and 20b of the hub system 12, the physical environment facing camera 113 may be a depth camera as well as a visible light sensitive camera. For example, the depth camera may include an IR illuminator transmitter and a hot reflecting surface like a hot mirror in front of the visible image sensor which lets the visible light pass and directs reflected IR radiation within a wavelength range or about a predetermined wavelength transmitted by the illuminator to a CCD or other type of depth sensor. The data from the sensors may be sent to a processor 210 of the control circuitry 13, or the processing unit 4,5 or both which may process them but which the unit 4,5 may also send to hub computing system 12 in some embodiments like FIG. 1A or over a network to one or more computer systems (e.g. like hub computing system 12) for processing. The processing identifies and maps the user's real world field of view. Additionally, the physical environment facing camera 113 may also include a light meter for measuring ambient light. A change of a certain amount may trigger a message for recalibration of training gaze data sets in some embodiments as discussed further below.

Control circuits 136 provide various electronics that support the other components of head mounted display device 2. More details of control circuits 136 are provided below with respect to FIG. 4A. Inside, or mounted to temple 102, are ear phones 130, inertial sensors 132, GPS transceiver 144 and temperature sensor 138. In one embodiment inertial sensors 132 include a three axis magnetometer 132A, three axis gyro 132B and three axis accelerometer 132C (See FIG. 4A). The inertial sensors are for sensing position, orientation, and sudden accelerations of head mounted display device 2. From these movements, head position may also be determined.

The display device 2 provides an image generation unit which can create one or more images including one or more virtual objects. In some embodiments, a microdisplay may be used as the image generation unit. A microdisplay assembly 173 comprises light processing elements and a variable focus adjuster 135. An example of a light processing element is a microdisplay unit 120. Other examples include one or more optical elements such as one or more lenses of a lens system 122 and one or more reflecting elements such as surfaces 124a and 124b in FIGS. 3A and 3B or 124 in FIGS. 3C and 3D. Lens system 122 may comprise a single lens or a plurality of lenses.

Mounted to or inside temple 102, the microdisplay unit 120 includes an image source and generates an image of a virtual object. The microdisplay unit 120 is optically aligned with the lens system 122 and the reflecting surface 124 or reflecting surfaces 124a and 124b as illustrated in the following figures. The optical alignment may be along an optical axis 133 or an optical path 133 including one or more optical axes. The microdisplay unit 120 projects the image of the virtual object through lens system 122, which may direct the image light, onto reflecting element 124 which directs the light into lightguide optical element 112 as in FIGS. 3C and 3D or onto reflecting surface 124a (e.g. a mirror or other surface) which directs the light of the virtual image to a partially reflecting element 124b which combines the virtual image view along path 133 with the natural or actual direct view along the optical axis 142 as in FIGS. 3A-3D. The combination of views are directed into a user's eye.

The variable focus adjuster 135 changes the displacement between one or more light processing elements in the optical path of the microdisplay assembly or an optical power of an element in the microdisplay assembly. The optical power of a lens is defined as the reciprocal of its focal length, e.g. 1/focal length, so a change in one effects the other. The change in focal length results in a change in the region of the field of view, e.g. a region at a certain distance, which is in focus for an image generated by the microdisplay assembly 173.

In one example of the microdisplay assembly 173 making displacement changes, the displacement changes are guided within an armature 137 supporting at least one light processing element such as the lens system 122 and the microdisplay 120 in this example. The armature 137 helps stabilize the alignment along the optical path 133 during physical movement of the elements to achieve a selected displacement or optical power. In some examples, the adjuster 135 may move one or more optical elements such as a lens in lens system 122 within the armature 137. In other examples, the armature may have grooves or space in the area around a light processing element so it slides over the element, for example, microdisplay 120, without moving the light processing element. Another element in the armature such as the lens system 122 is attached so that the system 122 or a lens within slides or moves with the moving armature 137. The displacement range is typically on the order of a few millimeters (mm). In one example, the range is 1-2 mm. In other examples, the armature 137 may provide support to the lens system 122 for focal adjustment techniques involving adjustment of other physical parameters than displacement. An example of such a parameter is polarization.

For more information on adjusting a focal distance of a microdisplay assembly, see U.S. patent Ser. No. 12/941,825 entitled "Automatic Variable Virtual Focus for Augmented Reality Displays," filed Nov. 8, 2010, having inventors Avi Bar-Zeev and John Lewis and which is hereby incorporated by reference.

In one example, the adjuster 135 may be an actuator such as a piezoelectric motor. Other technologies for the actuator may also be used and some examples of such technologies are a voice coil formed of a coil and a permanent magnet, a magnetostriction element, and an electrostriction element.

There are different image generation technologies that can be used to implement microdisplay 120. For example, microdisplay 120 can be implemented using a transmissive projection technology where the light source is modulated by optically active material, backlit with white light. These technologies are usually implemented using LCD type displays with powerful backlights and high optical energy densities. Microdisplay 120 can also be implemented using a reflective technology for which external light is reflected and modulated by an optically active material. The illumination is forward lit by either a white source or RGB source, depending on the technology. Digital light processing (DLP), liquid crystal on silicon (LCOS) and Mirasol® display technology from Qualcomm, Inc. are all examples of reflective technologies which are efficient as most energy is reflected away from the modulated structure and may be used in the system described herein. Additionally, microdisplay 120 can be implemented using an emissive technology where light is generated by the display. For example, a PicoP® engine from Microvision, Inc. emits a laser signal with a micro mirror steering either onto a tiny screen that acts as a transmissive element or beamed directly into the eye (e.g., laser).

As mentioned above, the configuration of the light processing elements of the microdisplay assembly 173 create a focal distance or focal region in which a virtual object appears in an image. Changing the configuration changes the focal region for the virtual object image. The focal region determined by the light processing elements can be determined and changed based on the equation $1/S_1 + 1/S_2 = 1/f$.

The symbol f represents the focal length of a lens such as lens system 122 in the microdisplay assembly 173. The lens system 122 has a front nodal point and a rear nodal point. If light rays are directed toward either nodal point at a given angle relative to the optical axis, the light rays will emerge from the other nodal point at an equivalent angle relative to the optical axis. In one example, the rear nodal point of lens system 122 would be between itself and the microdisplay 120. The distance from the rear nodal point to the microdisplay 120 may be denoted as S2. The front nodal point is typically within a few mm of lens system 122. The target location is the location of the virtual image to be generated by the microdisplay 120 in a three-dimensional physical space. The distance from the front nodal point to the target location of the virtual image may be denoted as S1. Since the image is to be a virtual image appearing on the same side of the lens as the microdisplay 120, sign conventions give that S1 has a negative value.

If the focal length of the lens is fixed, S1 and S2 are varied to focus virtual objects at different depths. For example, an initial position may have S1 set to infinity, and S2 equal to the focal length of lens system 122. Assuming lens system 122 has a focal length of 10 mm, consider an example in which the virtual object is to be placed about 1 foot or 300 mm into the user's field of view. S1 is now about −300 mm, f is 10 mm and S2 is set currently at the initial position of the focal length, 10 mm, meaning the rear nodal point of lens system 122 is 10 mm from the microdisplay 120. The new distance or new displacement between the lens 122 and microdisplay 120 is determined based on $1/(-300)+1/S2=1/10$ with all in units of mm. The result is about 9.67 mm for S2.

In one example, one or more processors such as in the control circuitry, the processing unit 4, 5 or both can calculate the displacement values for S1 and S2, leaving the focal length f fixed and cause the control circuitry 136 to cause a variable adjuster driver 237 (see FIG. 4A) to send drive signals to have the variable virtual focus adjuster 135 move the lens system 122 along the optical path 133 for example. In other embodiments, the microdisplay unit 120 may be moved instead or in addition to moving the lens system 122. In other embodiments, the focal length of at least one lens in the lens system 122 may be changed instead or with changes in the displacement along the optical path 133 as well.

Figure 3A:
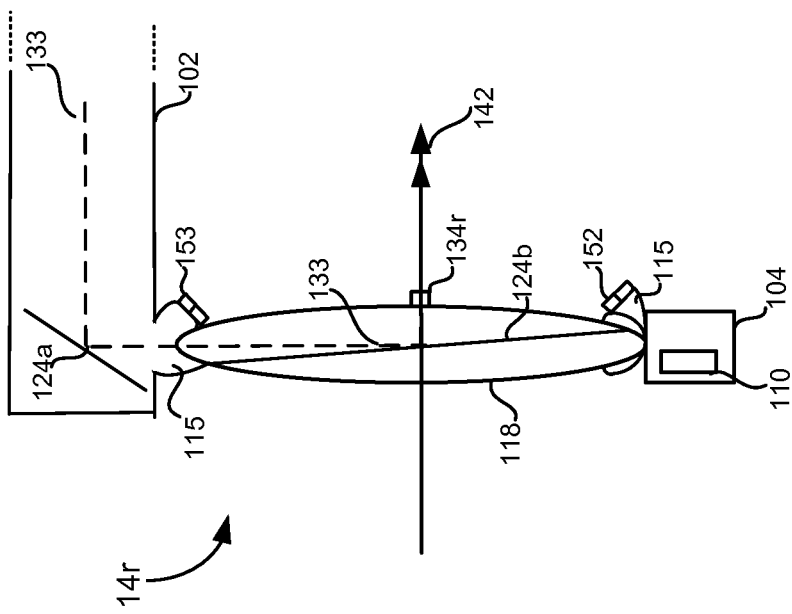
FIG. 3A is a top view of an embodiment of a display optical system of a see-through, near-eye, mixed reality device including an arrangement of gaze detection elements in a gaze detection system.

FIG. 3A is a top view of an embodiment of a display optical system 14 of a see-through, near-eye, mixed reality device including an arrangement of gaze detection elements in a gaze detection system. A portion of the frame 115 of the near-eye display device 2 will surround a display optical system including providing support for one or more lenses as illustrated. In order to show the components of the display system 14, in this case 14r for the right eye system, a top portion of the frame 115 surrounding the display optical system is not depicted.

The display optical system 14 in this embodiment has an optical axis 142 and includes a see-through lens 118 allowing the user an actual direct view of the real world. In this example, the see-through lens 118 is a standard lens used in eye glasses and can be made to any prescription (including no prescription). In another embodiment, see-through lens 118 can be replaced by a variable prescription lens. In some embodiments, see-through, near-eye display device 2 will include additional lenses.

The display optical system 14 further comprises reflecting surfaces 124a and 124b. In this embodiment, light from the microdisplay 120 is directed along optical path 133 via a reflecting element 124a to a partially reflective element 124b embedded in lens 118 which combines the virtual object image view traveling along optical path 133 with the natural or actual direct view along the optical axis 142 so that the combined views are directed into a user's eye, right one in this example, at the optical axis, the position with the most collimated light for a clearest view.

A detection area 139r of a light sensor is also part of the display optical system 14r. An optical element 125 embodies the detection area 139r by capturing reflected light from the user's eye received along the optical axis 142 and directs the captured light to the sensor 134r, in this example positioned in the bridge 104. As shown, the arrangement allows the detection area 139 of the sensor 134r to have its center aligned with the center of the display optical system 14. For example, if sensor 134r is an image sensor, sensor 134r captures the detection area 139, so an image captured at the image sensor is centered on the optical axis because the detection area 139 is. In one example, sensor 134 r is a visible light camera or a combination of RGB/IR camera, and the optical element 125 includes an optical element which reflects visible light reflected from the user's eye, for example a partially reflective mirror.

In other embodiments, the sensor 134r is an IR sensitive device such as an IR camera, and the element 125 includes a hot reflecting surface which lets visible light pass through it and reflects IR radiation to the sensor 134r. An IR camera may capture not only glints, but also an infra-red or near-infra-red image of the user's eye including the pupil.

In other embodiments, the IR sensor device 134r is a position sensitive device (PSD), sometimes referred to as an optical position sensor. The position of detected light on the surface of the sensor is identified. A PSD can be selected which is sensitive to a wavelength range or about a predetermined wavelength of IR illuminators for the glints. When light within the wavelength range or about the predetermined wavelength of the position sensitive device is detected on the sensor or light sensitive portion of the device, an electrical signal is generated which identifies the location on the surface of the detector. In some embodiments, the surface of a PSD is divided into discrete sensors like pixels from which the location of the light can be determined. In other examples, a PSD isotropic sensor may be used in which a change in local resistance on the surface can be used to identify the location of the light spot on the PSD. Other embodiments of PSDs may also be used. By operating the illuminators 153 in a predetermined sequence, the location of the reflection of glints on the PSD can be identified and hence related back to their location on a cornea surface.

The depiction of the light directing elements, in this case reflecting elements, 125, 124, 124a and 124b in FIGS. 3A-3D are representative of their functions. The elements may take any number of forms and be implemented with one or more optical components in one or more arrangements for directing light to its intended destination such as a camera sensor or a user's eye.

The display optical system 14 includes other gaze detection elements in this embodiment. In this embodiment, attached to frame 115 and on the sides of lens 118, are at least two (2) but may be more, infra-red (IR) illuminating devices 153 which direct narrow infra-red light beams within a particular wavelength range or about a predetermined wavelength at the user's eye to each generate a respective glint on a surface of the respective cornea. In other embodiments, the illuminators and any photodiodes may be on the lenses, for example at the corners or edges. In this embodiment, in addition to the at least 2 infra-red (IR) illuminating device 153 are IR photodetectors 152. Each photodetector 152 is sensitive to IR radiation within the particular wavelength range of its corresponding IR illuminator 153 across the lens 118 and is positioned to detect a respective glint. As shown in FIGS. 1C-1E, the illuminator and photodetector are separated by a barrier 154 so that incident IR light from the illuminator 153 does not interfere with reflected IR light being received at the photodetector 152. In the case where the sensor 134 is an IR sensor, the photodetectors 152 may not be needed or may be an additional glint data capture source. With a visible light camera, the photodetectors 152 capture light from glints and generate glint intensity values.

Figure 3B:
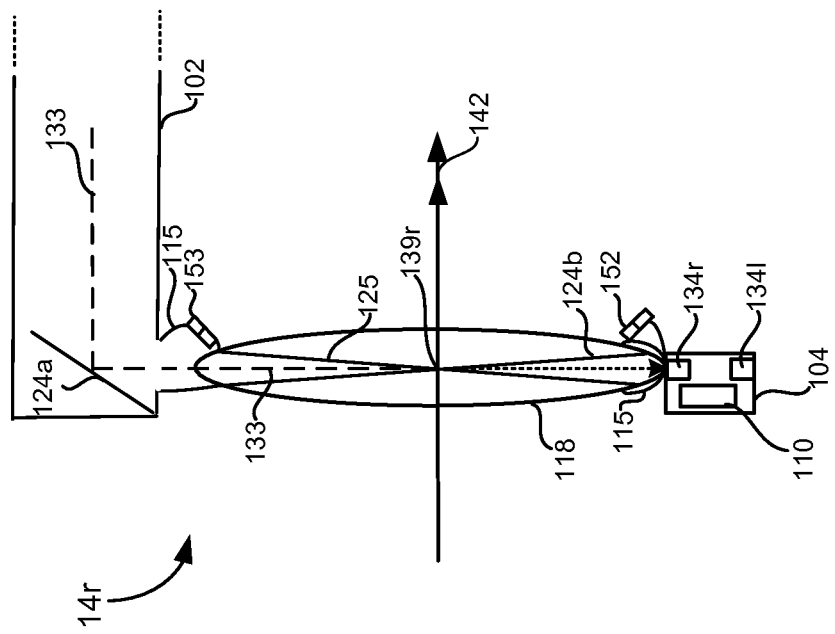
FIG. 3B is a top view of another embodiment of a display optical system of a see-through, near-eye, mixed reality device including an arrangement of gaze detection elements in a gaze detection system.

FIG. 3B is a top view of another embodiment of a display optical system 14 of a see-through, near-eye, mixed reality device including an arrangement of gaze detection elements in a gaze detection system. In this embodiment, in addition to the at least 2 infra-red (IR) illuminating devices 153 are IR photodetectors 152. In this embodiment, the hot reflecting surface 125 has been removed to show operation without a position sensitive detector.

In the embodiment of FIG. 3B, light detector 134*r* may be embodied as a visible light camera, sometimes referred to as an RGB camera, or it may be embodied as an IR camera or a camera capable of processing light in both the visible and IR ranges e.g. a depth camera. In this example, the image sensor 134*r* is the detection area 139*r*, and the image sensor 134 of the camera is located vertically on the optical axis 142 of the display optical system. In some examples, the camera may be located on frame 115 either above or below see-through lens 118 or embedded in the lens 118. In some embodiments, the illuminators 153 provide light for the camera, and in other embodiments the camera captures images with ambient lighting or light from its own light source.

In one embodiment, glint reflections can estimate gaze based on a few data points of the intensity values detected for the glints, rather than processing much, much larger sets of image data of eyes. The position of the illuminators 153 on the eyeglass frame 115 or other support structure of a near-eye display device may be fixed so that the position of glints detected by one or more sensors is fixed in the sensor detection area. The cornea and hence the iris and the pupil rotate with the eyeball about a fixed center. The iris, pupil, and the sclera which is sometimes referred to as the white portion of the eyeball, move underneath the glint as the user's gaze changes. So a glint detected at a same sensor location may result in different intensity values due to different reflectivities associated with the different eye parts. As the pupil is a hole with tissue that absorbs most incoming light, the intensity value for it would be very low or near zero, while that for the iris would be a higher intensity value due to its higher reflectivity. An intensity value for the sclera may be highest as the sclera has the highest reflectivity. In some examples, an illuminator may be positioned as in FIGS. 3A through 3D on either side of the display optical system 14 and hence on either side of the pupil of the user's eye. In other embodiments, additional illuminators may be positioned on the frame 115 or lens 118, for example, four illuminators may be positioned to generate a surrounding geometric shape, e.g. a box, of glints on the eyeball which would be approximately centered on the pupil when a user is looking straight ahead. The microdisplay assembly 173 can display a virtual image or send a message, e.g. a visual virtual image or an audio instruction to a user to cause the user to look straight ahead for initializing the glints on or near the pupil. In other embodiments, gaze detection based on glints is based on intensity values generated from illuminators with the glint positioning being independent of being centered on the pupil.

FIG. 3C is a top view of a third embodiment of a display optical system 14 of a see-through, near-eye, mixed reality device including an arrangement of gaze detection elements in a gaze detection system. The display includes a light guide optical element 112 between an additional see-through lens 116 and see-through lens 118. Lightguide optical element 112 channels artificial light to the eye.

Lightguide optical element 112 transmits light from microdisplay 120 to the eye of the user wearing head mounted display device 2. Lightguide optical element 112 also allows light from in front of the head mounted display device 2 to be transmitted through lightguide optical element 112 to the user's eye thereby allowing the user to have an actual direct view of the space in front of head mounted display device 2 in addition to receiving a virtual image from microdisplay 120. Thus, the walls of lightguide optical element 112 are see-through. Lightguide optical element 112 includes a first reflecting surface 124 (e.g., a mirror or other surface). Light from microdisplay 120 passes through lens 122 and becomes incident on reflecting surface 124. The reflecting surface 124 reflects the incident light from the microdisplay 120 such that light is trapped inside a planar, substrate comprising lightguide optical element 112 by internal reflection.

After several reflections off the surfaces of the substrate, the trapped light waves reach an array of selectively reflecting surfaces 126. Note that only one of the five surfaces is labeled 126 to prevent over-crowding of the drawing. Reflecting surfaces 126 couple the light waves incident upon those reflecting surfaces out of the substrate into the eye of the user. More details of a lightguide optical element can be found in United States Patent Application Publication 2008/0285140, Ser. No. 12/214,366, published on Nov. 20, 2008, "Substrate-Guided Optical Devices" incorporated herein by reference in its entirety.

In this embodiment, as in FIG. 1E and one of the examples for FIG. 3B, the display optical system 14 is similarly arranged with IR illuminators 153 and photodetectors 152, and a visible light or IR camera 134*r* located on the frame 115 or lens 118 below or above optical axis 142, typically at a center of lenses 116 and 118 supporting the lightguide optical element 112.

FIG. 3D is a top view of a fourth embodiment of a display optical system 14 of a see-through, near-eye, mixed reality device including an arrangement of gaze detection elements in a gaze detection system. This embodiment is similar to FIG. 3C's embodiment including a light guide optical element 112. However, the only light detectors are the IR photodetectors 152, so this embodiment relies on glint detection only for gaze detection as discussed in the examples below.

In the embodiments of FIGS. 3A-3D, the positions of the gaze detection elements, e.g. the detection area 139 and the illuminators 153 and photodetectors 152 are fixed with respect to each other. In these examples, they are also fixed in relation to the optical axis of the display optical system 14.

In the embodiments above, the specific number of lenses shown are just examples. Other numbers and configurations of lenses operating on the same principles may be used. Additionally, in the examples above, only the right side of the see-through, near-eye display 2 are shown. A full near-eye, mixed reality display device would include as examples another set of lenses 116 and/or 118, another lightguide optical element 112 for the embodiments of FIGS. 3C and 3D, another micro display 120, another lens system 122, likely another environment facing camera 113, another eye tracking camera 134 for the embodiments of FIGS. 3A to 3C, earphones 130, and a temperature sensor 138.

Figure 4A:
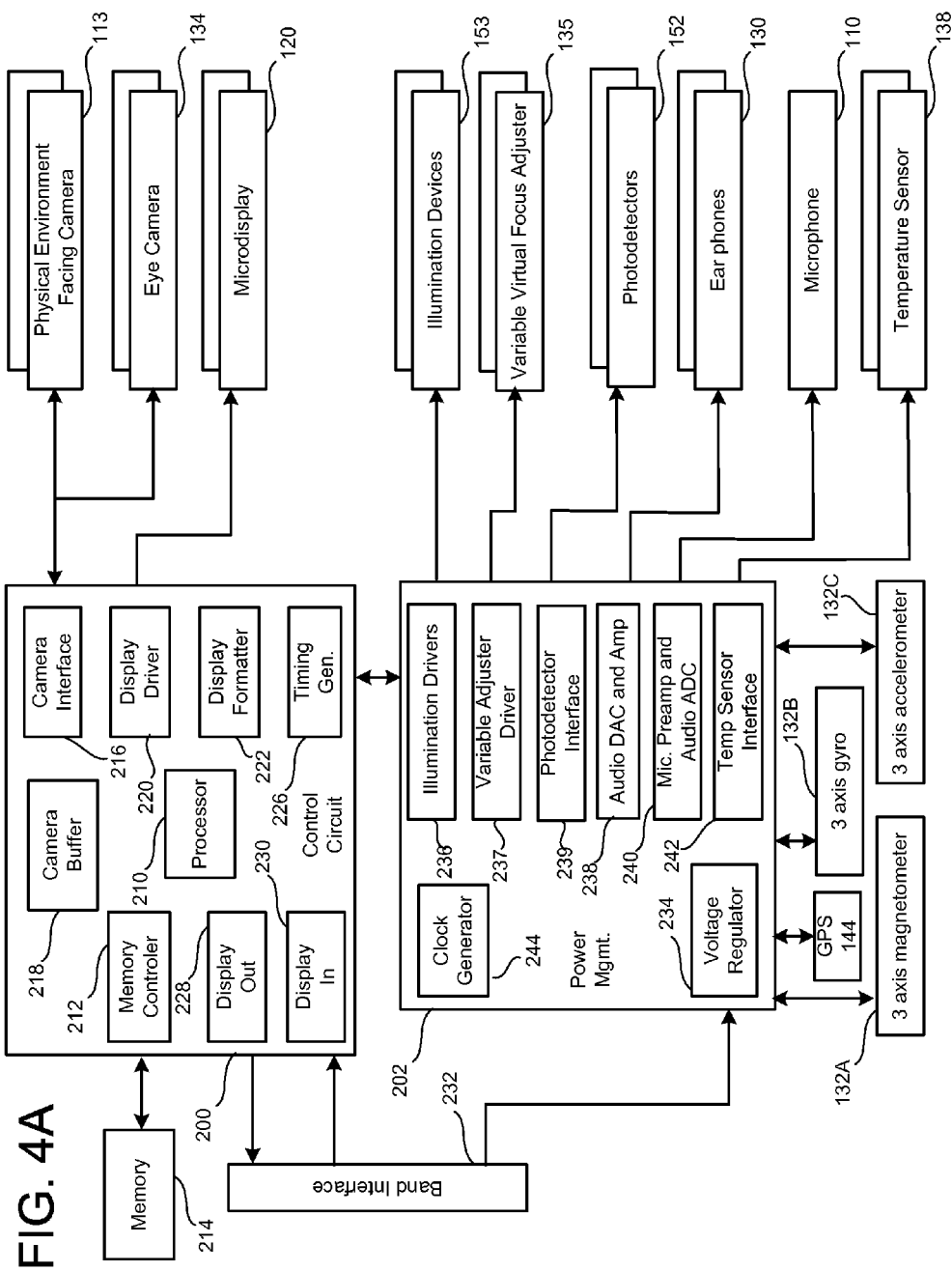
FIG. 4A is a block diagram of one embodiment of hardware and software components of a see-through, near-eye, mixed reality display unit as may be used for the embodiment of FIG. 2.

FIG. 4A is a block diagram of one embodiment of hardware and software components of a see-through, near-eye, mixed reality display unit as may be used with the embodiments described in this disclosure. FIG. 4B is a block diagram describing the various components of processing unit 4. In this embodiment, near-eye display device 2, receive instructions about a virtual image from processing unit 4 and provides the sensor information back to processing unit 4. Processing unit 4, the components of which are depicted in FIG. 4B, will receive the sensory information from the display device 2 and may also receive sensory information from hub computing device 12 (See FIG. 1). Based on that information, processing unit 4 will determine where and when to provide a virtual image to the user and send instructions accordingly to the control circuitry 136 of the display device 2.

Note that some of the components of FIG. 4A (e.g., physical environment facing camera 113, eye camera 134, variable virtual focus adjuster 135, photodetector interface 139, micro display 120, illumination device 153 or illuminators, earphones 130, and temperature sensor 138) are shown in shadow to indicate that there are two of each of those devices, one for the left side and one for the right side of head mounted display device 2. FIG. 4A shows the control circuit 200 in communication with the power management circuit 202. Control circuit 200 includes processor 210, memory controller 212 in communication with memory 214 (e.g., D-RAM), camera interface 216, camera buffer 218, display driver 220, display formatter 222, timing generator 226, display out interface 228, and display in interface 230. In one embodiment, all of components of control circuit 220 are in communication with each other via dedicated lines of one or more buses. In another embodiment, each of the components of control circuit 200 are in communication with processor 210.

Camera interface 216 provides an interface to the two physical environment facing cameras 113 and each eye camera 134 and stores respective images received from the cameras 113, 134 in camera buffer 218. Display driver 220 will drive microdisplay 120. Display formatter 222 may provide information, about the virtual image being displayed on microdisplay 120 to one or more processors of one or more computer systems, e.g. 4, 12, 210 performing processing for the augmented reality system. Timing generator 226 is used to provide timing data for the system. Display out 228 is a buffer for providing images from physical environment facing cameras 113 and the eye cameras 134 to the processing unit 4. Display in 230 is a buffer for receiving images such as a virtual image to be displayed on microdisplay 120. Display out 228 and display in 230 communicate with band interface 232 which is an interface to processing unit 4.

Power management circuit 202 includes voltage regulator 234, eye tracking illumination driver 236, variable adjuster driver 237, photodetector interface 239, audio DAC and amplifier 238, microphone preamplifier and audio ADC 240, temperature sensor interface 242 and clock generator 244. Voltage regulator 234 receives power from processing unit 4 via band interface 232 and provides that power to the other components of head mounted display device 2. Illumination driver 236 controls, for example via a drive current or voltage, the illumination devices 153 to operate about a predetermined wavelength or within a wavelength range. Audio DAC and amplifier 238 receives the audio information from earphones 130. Microphone preamplifier and audio ADC 240 provides an interface for microphone 110. Temperature sensor interface 242 is an interface for temperature sensor 138. Power management unit 202 also provides power and receives data back from three axis magnetometer 132A, three axis gyro 132B and three axis accelerometer 132C. Power management unit 202 also provides power and receives data back from and sends data to GPS transceiver 144.

The variable adjuster driver 237 provides a control signal, for example a drive current or a drive voltage, to the adjuster 135 to move one or more elements of the microdisplay assembly 173 to achieve a displacement for a focal region calculated by software executing in the a processor 210 of the control circuitry 13, or the processing unit 4,5 or the hub computer 12 or both. In embodiments of sweeping through a range of displacements and, hence, a range of focal regions, the variable adjuster driver 237 receives timing signals from the timing generator 226, or alternatively, the clock generator 244 to operate at a programmed rate or frequency.

The photodetector interface 239 performs any analog to digital conversion needed for voltage or current readings from each photodetector, stores the readings in a processor readable format in memory via the memory controller 212, and monitors the operation parameters of the photodetectors 152 such as temperature and wavelength accuracy.

FIG. 4B is a block diagram of one embodiment of the hardware and software components of a processing unit 4, 5 associated with a see-through, near-eye display unit. The mobile device 5 may include this embodiment of hardware and software components as well or similar components which perform similar functions. FIG. 4B shows controls circuit 304 in communication with power management circuit 306. Control circuit 304 includes a central processing unit (CPU) 320, graphics processing unit (GPU) 322, cache 324, RAM 326, memory control 328 in communication with memory 330 (e.g., D-RAM), flash memory controller 332 in communication with flash memory 334 (or other type of non-volatile storage), display out buffer 336 in communication with see-through, near-eye display device 2 via band interface 302 and band interface 232, display in buffer 338 in communication with near-eye display device 2 via band interface 302 and band interface 232, microphone interface 340 in communication with an external microphone connector 342 for connecting to a microphone, PCI express interface for connecting to a wireless communication device 346, and USB port(s) 348.

In one embodiment, wireless communication component 346 can include a Wi-Fi enabled communication device, Bluetooth communication device, infrared communication device, etc. The USB port can be used to dock the processing unit 4, 5 to hub computing device 12 in order to load data or software onto processing unit 4, 5, as well as charge processing unit 4, 5. In one embodiment, CPU 320 and GPU 322 are the main workhorses for determining where, when and how to insert virtual images into the view of the user.

Power management circuit 306 includes clock generator 360, analog to digital converter 362, battery charger 364, voltage regulator 366, see-through, near-eye display power source 376, and temperature sensor interface 372 in communication with temperature sensor 374 (located on the wrist band of processing unit 4). An alternating current to direct current converter 362 is connected to a charging jack 370 for receiving an AC supply and creating a DC supply for the system. Voltage regulator 366 is in communication with battery 368 for supplying power to the system. Battery charger 364 is used to charge battery 368 (via voltage regulator 366) upon receiving power from charging jack 370. Device power interface 376 provides power to the display device 2.

FIG. 5 is a top view illustrating examples of gaze vectors intersecting at a point of gaze where a user's eyes are focused. A model of the eye 160*l*, 160*r* is illustrated for each eye based on the Gullstrand schematic eye model. For each eye, an eyeball 160 is modeled as a sphere with a center of rotation 166 and includes a cornea 168 modeled as a sphere too and having a center 164. The cornea rotates with the eyeball, and the center 166 of rotation of the eyeball may be treated as a fixed point. The cornea covers an iris 170 with a pupil 162 at its center. In this example, on the surface 172 of the respective cornea are glints 174 and 176.

The axis 178 formed from the center of rotation 166 through the cornea center 164 to the pupil 162 is the optical axis of the eye. A gaze vector 180 is sometimes referred to as the line of sight or visual axis which extends from the fovea through the center of the pupil 162. The fovea is a small area of about 1.2 degrees located in the retina. The angular offset between the optical axis computed in the embodiment of FIG. 9 and the visual axes has horizontal and vertical components. The horizontal component is up to 5 degrees from the optical axis, and the vertical component is between 2 and 3 degrees. In many embodiments, the optical axis is determined and a small correction determined through user calibration is applied to obtain the visual axis which is selected as the gaze vector. For each user, a small virtual object may be displayed by the display device at each of a number of predetermined positions at different horizontal and vertical positions. An optical axis may be computed for during display of the object at each position, and a ray modeled as extending from the position into the user eye. An offset angle with horizontal and vertical components may be determined based on how the optical axis must be moved to align with the modeled ray. From the different positions, an average offset angle with horizontal or vertical components can be selected as the small correction to be applied to each computed optical axis. In some embodiments, only a horizontal component is used for the offset angle correction.

In the illustrated embodiment of FIG. 5, a sensor detection area 139 is aligned with the optical axis of each display optical system 14 within an eyeglass frame 115. The respective image sensor in this example is a camera capable of capturing image data representing glints 174*l* and 176*l* generated respectively by illuminators 153*a* and 153*b* on the left side of the frame 115 and data representing glints 174*r* and 176*r* generated respectively by illuminators 153*c* and 153*d*.

Through the display optical systems, 14*l* and 14*r* in the eyeglass frame 115, the user's field of view includes both real objects 190, 192 and 194 and virtual objects 182, 184, and 186. In this example, the cornea 168*l* of the left eye is rotated to the right or towards the user's nose, and the cornea 168*r* of the right eye is rotated to the left or towards the user's nose. Both pupils are gazing at a virtual object 186. Gaze vectors 180*l* and 180*r* from each eye enter the Panum's fusional region 195 in which virtual object 186 is located. The Panum's fusional region is the area of single vision in a binocular viewing system like that of human vision. The intersection of the gaze vectors 180*l* and 180*r* indicates that the user is looking at virtual object 186.

For a see-through mixed reality display device, the gaze vectors are determined to identify a point of gaze in a three-dimensional (3D) user field of view which includes both real objects, typically not under computer control, and virtual objects generated by an application. The gaze vectors may intersect at an object 10 feet away or at a distance effectively at infinity. The following figures briefly discuss embodiments for determining a 3D user field of view.

References to front facing image data are referring to image data from one or more front facing camera like camera 113 in FIGS. 1A and 1B. In these embodiments, the field of view of the front facing cameras 113 approximates the user field of view as the camera is located at a relatively small offset from the optical axis 142 of each display optical system 14. The offset may be taken into account in the image data.

Figure 6A:
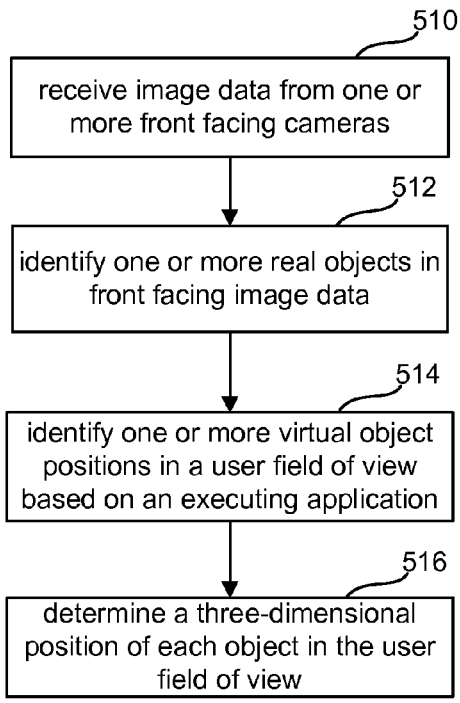
FIG. 6A is a flowchart of a method embodiment for determining a three-dimensional user field of view.

FIG. 6A is a flowchart of a method embodiment for determining a three-dimensional user field of view. In step 510, one or more processors of the control circuitry 136, the processing unit 4,5, the hub computing system 12 or a combination of these receive image data from one or more front facing cameras, and in step 512 identify one or more real objects in front facing image data. Data from the orientation sensor 132, e.g. the three axis accelerometer 132C and the three axis magnetometer 132A, can also be used with the front facing camera 113 image data for mapping what is around the user, the position of the user's face and head in order to determine which objects, real or virtual, he or she is likely focusing on at the time. Based on an executing application, the one or more processors in step 514 identify virtual object positions in a user field of view which may be determined to be the field of view captured in the front facing image data. In step 516, a three-dimensional position is determined for each object in the user field of view. In other words, where each object is located with respect to the display device 2, for example with respect to the optical axis 142 of each display optical system 14.

Figure 6B:
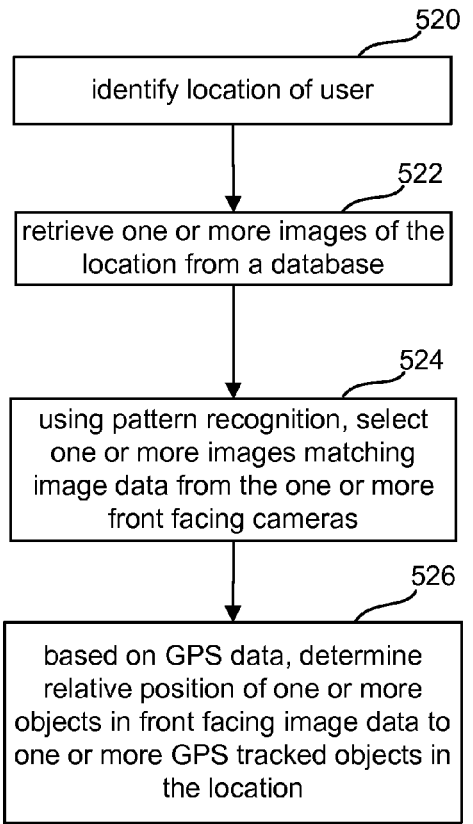
FIG. 6B is a flowchart of a method embodiment for identifying one or more real objects in a user field of view.

FIG. 6B is a flowchart of a method embodiment for identifying one or more real objects in a user field of view. This embodiment may be used to implement step 512. Each of the implementing examples in FIGS. 6B, 6D and 6E may be used separately or in conjunction with one another to identify the location of objects in the user field of view. In step 520, a location of user wearing the display device 2 is identified. For example, GPS data via a GPS unit 965 in the mobile device 5 or GPS transceiver 144 on the display device 2 may identify the location of the user. In step 522, one or more processors, retrieve one or more images of the location from a database (e.g. 470), and uses pattern recognition in step 524 to select one or more images matching image data from the one or more front facing cameras. In some embodiments, steps 522 and 524 may be performed remotely by a more powerful computer, e.g. hub 12, having access to image databases. Based on GPS data, in step 526 the one or more processors determines a relative position of one or more objects in front facing image data to one or more GPS tracked objects 528 in the location, and determines in step 529 a position of user from the one or more real objects based on the one or more relative positions.

Figure 6C:
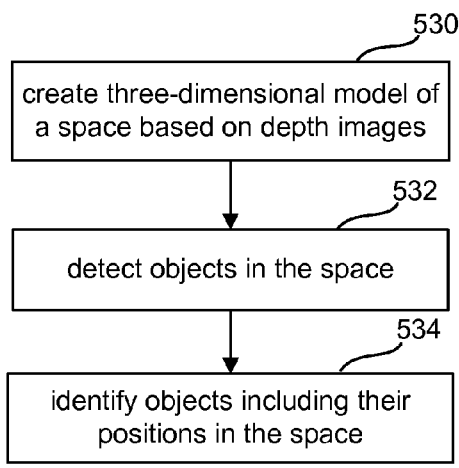
FIG. 6C is a flowchart of a method embodiment for generating a three-dimensional model of a user space.

In some embodiments such as in FIG. 1A, a user wearing a see-through, near-eye display may be in a location in which a computer system or one or more computers provides a three-dimensional mapping of objects within a space, e.g. a store. FIG. 6C is a flowchart of a method embodiment for generating a three-dimensional model of a user space. In step 530, a computer system with access to depth cameras like hub system 12 with capture devices 20A and 20B creates a three-dimensional model of a space based on depth images. The depth images may be from multiple perspectives and may be combined based on a common coordinate space, e.g. the store space, and creates a volumetric or three dimensional description of the space. In step 532, objects are detected in the space. For example, edge detection may be performed on the depth images to distinguish objects, including people, from each other. In step 534, the computer system 12 identifies one or more detected objects including their positions in the space. The objects may also be identified based on comparisons of shape and pattern recognition techniques including facial recognition techniques with reference images of things and people from image databases.

Figures 6D, 6E:
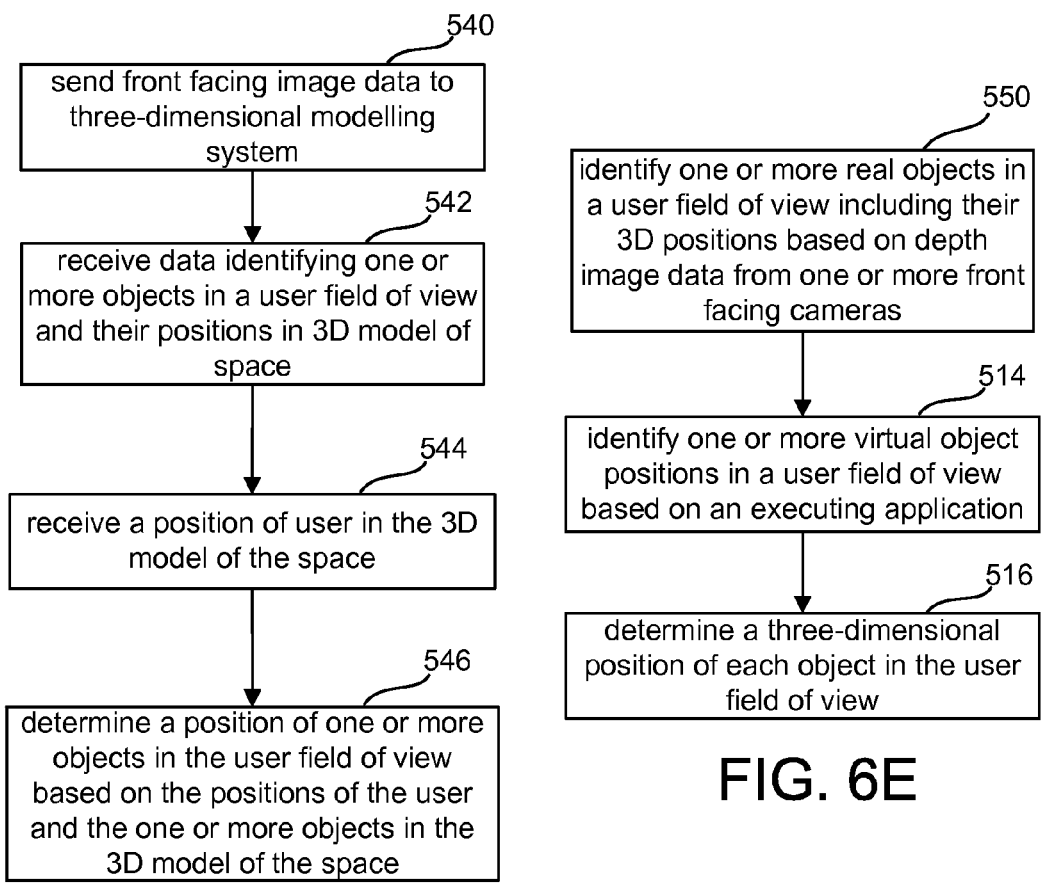
FIG. 6D is a flowchart of a method embodiment for identifying one or more objects in a user field of view.
FIG. 6E is a flowchart of a method embodiment for identifying one or more objects in a user field of view.

FIG. 6D is a flowchart of a method embodiment for identifying one or more objects in a user field of view based on depth data transmitted to the see-through, mixed reality display device 2. The processing unit 4,5 in step 540 sends front facing image data to a three-dimensional modeling system such as may be implemented by a depth image processing application executing on a computer system like hub computing system 12 communicatively coupled to depth cameras 20A and 20B. Data from the orientation sensor 132 may also be sent for identifying face or head position. For example, when a user enters a store, a computer system at the store provides a 3D mapping of the store and what and who is in it. In step 542, the display device 2 receives data identifying one or more objects in a field of view for the user and their positions in a 3D model of a space. The image data from the one or more front facing cameras 113 approximates the user field of view, so the hub system 12 identifies the object in the front facing image data, for example through image recognition or pattern recognition software. Orientation data may also be used with the front facing image data to refine the user field of view and identify objects tracked by the computer system 12 falling within the user field of view. (The hub system 12 also aligns the front facing image data when received from two or more cameras 113 for identifying the user field of view.) The processing unit 4,5 in step 544 receives a position of the user in the 3D model of the space, and in step 546 the processing unit 4,5, or the processor 210 of the control circuitry 136 or both determines a position of one or more objects in the user field of view based on the positions of the user and the one or more objects in the 3D model of the space. In another example, the processing unit 4,5 receives the position of the user and the one or more objects as determined by the computer system 12.

FIG. 6E is a flowchart of a method embodiment for identifying one or more objects in a user field of view when the front facing camera 113 is a depth camera providing depth image data or has a depth sensor for providing depth data which can be combined with image data to provide depth image data. In step 550, the one or more processors of the display device 2, e.g. processor 210 of the control circuitry or the processing unit 4,5, or both identifies one or more real objects in a user field of view including their three-dimensional positions based on depth image data from one or more front facing cameras. The one or more processors may also map the user field of view based on orientation data from an orientation sensor 132 in addition to the image data. The one or more processors perform step 514 of identifying virtual object positions in the user field of view based on an executing application and step 516 of determining a three-dimensional position of each object in the user field of view. Additionally, a remote computer system 12 may also providing additional processing power to the other processors for performing the steps of FIG. 6E.

Each of the method embodiments of FIGS. 6A through 6E are typically performed repeatedly as the user and objects within the user's environment move around.

Figure 6F:
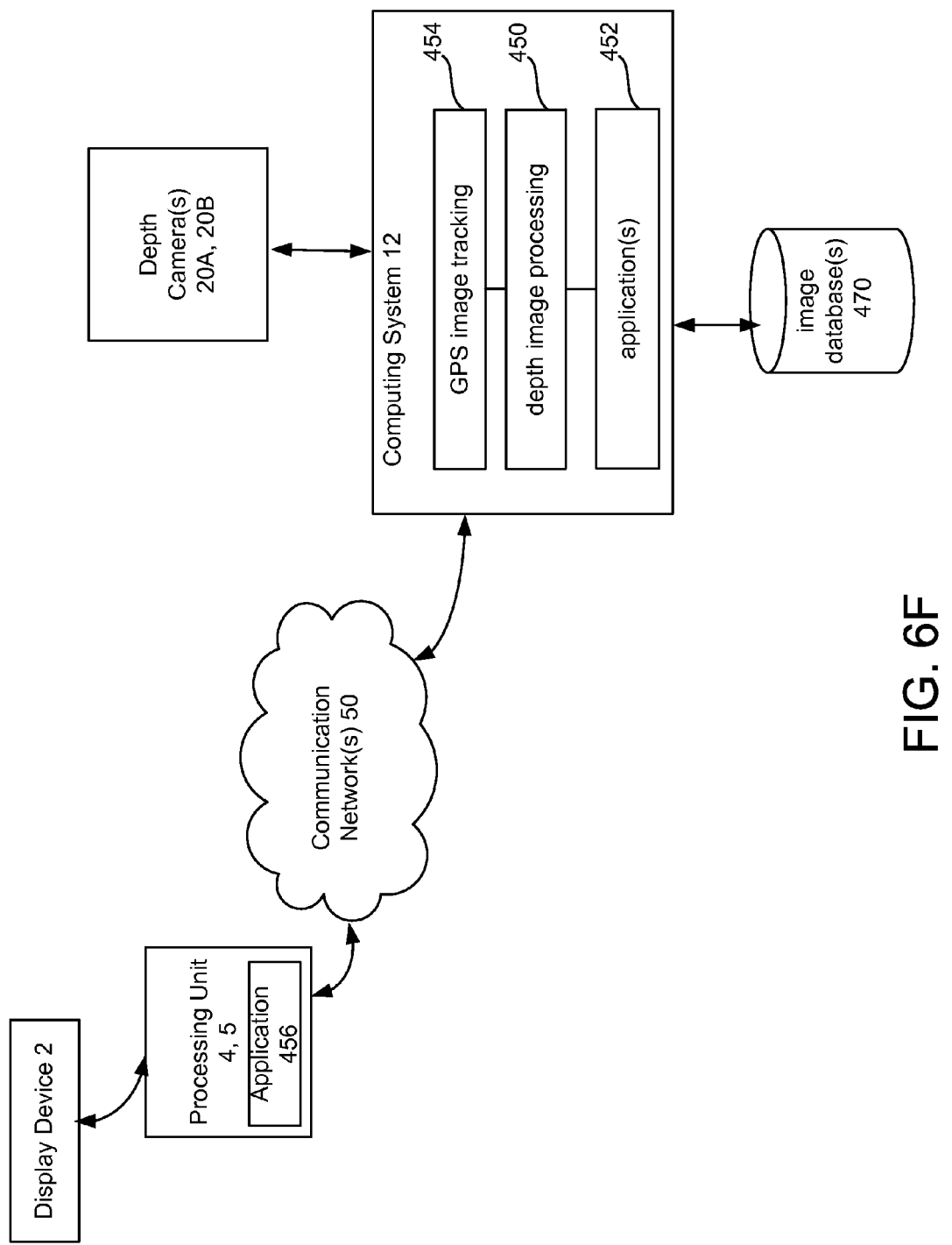
FIG. 6F is a block diagram of a system embodiment for determining positions of objects within a user field of view of a see-through, near-eye display device.

FIG. 6F is a block diagram of a system embodiment for determining positions of objects within a user field of view of a see-through, near-eye display device. This embodiment illustrates how the various devices may leverage networked computers to map a three-dimensional model of a user field of view and the real and virtual objects within the model. An application 456 executing in a processing unit 4,5 communicatively coupled to a display device 2 can communicate over one or more communication networks 50 with a computing system 12 for processing of image data to determine and track a user field of view in three dimensions. The computing system 12 may be executing an application 452 remotely for the processing unit 4,5 for providing images of one or more virtual objects. Either or both of the applications 456 and 452 working together may map a 3D model of space around the user. A depth image processing application 450 detects objects, identifies objects and their locations in the model. The application 450 may perform its processing based on depth image data from depth camera like 20A and 20B, two-dimensional or depth image data from one or more front facing cameras 113, and GPS metadata associated with objects in the image data obtained from a GPS image tracking application 454.

The GPS image tracking application 454 identifies images of the user's location in one or more image database(s) 470 based on GPS data received from the processing unit 4,5 or other GPS units identified as being within a vicinity of the user, or both. Additionally, the image database(s) may provide accessible images of a location with metadata like GPS data and identifying data uploaded by users who wish to share their images. The GPS image tracking application provides distances between objects in an image based on GPS data to the depth image processing application 450. Additionally, the application 456 may perform processing for mapping and locating objects in a 3D user space locally and may interact with the GPS image tracking application for receiving distances between objects. Many combinations of shared processing are possible between the applications by leveraging network connectivity.

Figure 7:
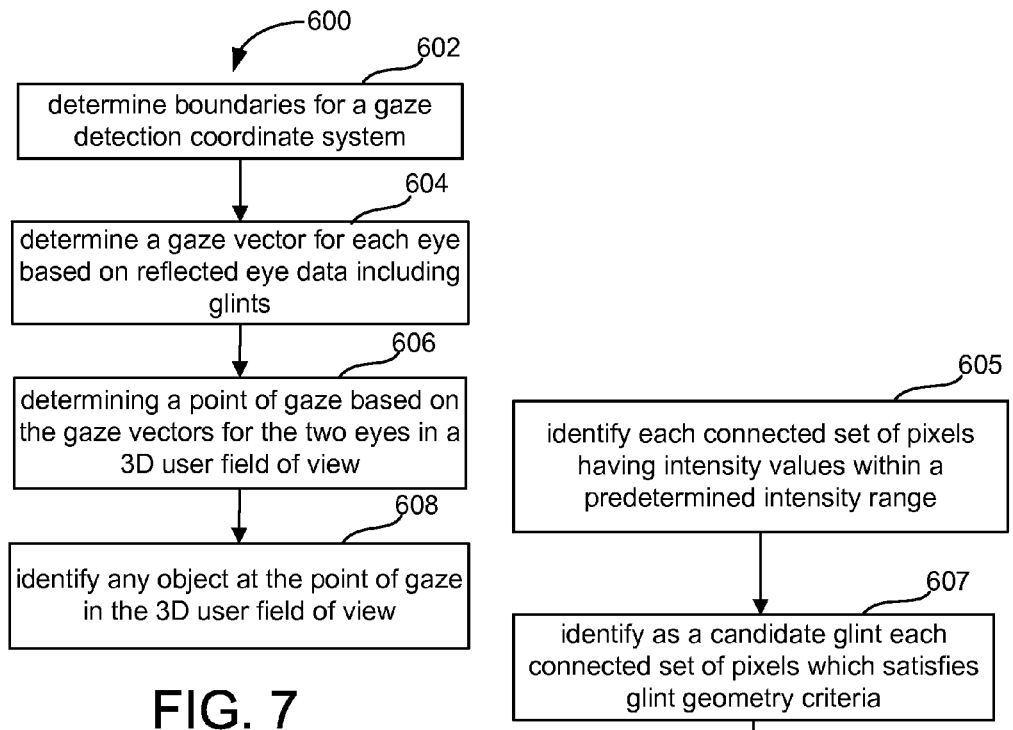
FIG. 7 is a flowchart of a method embodiment for determining gaze in a see-through, near-eye mixed reality display system.

FIG. 7 is a flowchart of a method embodiment for determining gaze in a see-through, near-eye mixed reality display system and provides an overall view of how a near-eye display device can leverage its geometry of optical components to determine gaze. One or more processors such as that in processing unit 4, the mobile device 5, the control circuitry 136, or the hub computing system 12 alone or in combination 12 determine in step 602 boundaries for a gaze detection coordinate system. In step 604, a gaze vector for each eye is determined based on reflected eye data including glints, and in step 606 a point of gaze, e.g. what the user is looking at, is determined for the two eyes in a three-dimensional (3D) user field of view. As the positions and identity of objects in the user field of view are tracked, for example, by embodiments like in FIGS. 6A-6F, in step 608, any object at the point of gaze in the 3D user field of view is identified. In many embodiments, the three-dimensional user field of view includes displayed virtual objects and an actual direct view of real objects. The term object includes a person.

Figure 8:
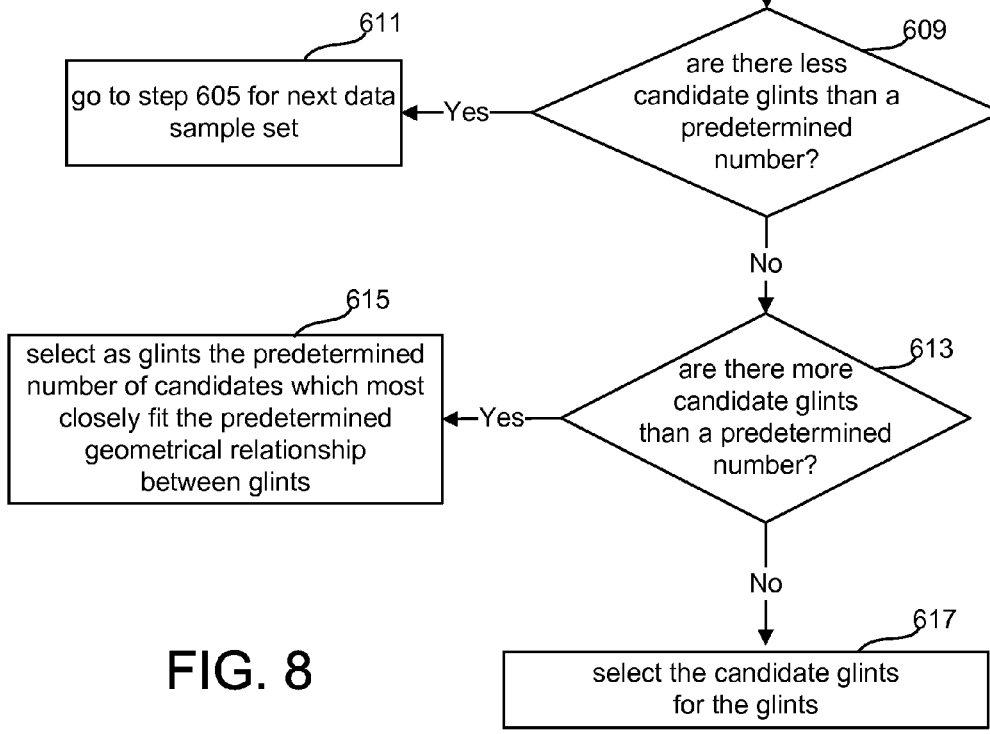
FIG. 8 is a flowchart of a method embodiment for identifying glints in image data.

The method embodiment in FIG. 7 and other method embodiments discussed below which use glint data for other ways of detecting gaze, may identify such glints from image data of the eye. When IR illuminators are used, typically an IR image sensor is used as well. The following method may also work with a discrete surface position sensitive detector (PSD), e.g. one with pixels. FIG. 8 is a flowchart of a method embodiment for identifying glints in image data. As noted above, a glint is a very small and a very bright reflection of light from a light source off of a specularly reflective surface such as the cornea of an eye. In the method embodiment below, each of the steps is performed for a data sample set. In some examples, that may include data from one image or image frame, and in others, the data sample set may be for a number of images or image frames. In step 605, the processor identifies each connected set of pixels having their intensity values within a predetermined intensity range, for example, the range of intensity values may begin at 220 and end at the brightest pixel value 255. In step 607, the candidate glints are pruned by identifying as a candidate glint each connected set of pixels which satisfies glint geometry criteria. An example of glint geometry criteria is size and shape for the glints. Some may be too large, too small, or have too irregular a shape. Furthermore, the illuminators are positioned for the resulting glints to have a spatial or geometric relationship to each other. For example, the illuminators 153 are arranged for the glints to form a rectangle. In the embodiment discussed in FIG. 9 in which a pupil center is determined from image data as well, a spatial relationship to the pupil may also be a criteria, e.g. a distance too far from the pupil may indicate a connected set is not a candidate glint.

In step 609, the one or more processors determine whether there are less candidate glints than a predetermined number. For example, for four illuminators, four glints are expected but the predetermined number may be two. In the example of the rectangle as the geometric relationship, two glints which form a horizontal line or a diagonal line of a predetermined length may have been selected as candidates. There may be an eyelid or eyelash obstruction for the other glints. If there are less than the predetermined number of glints, the data sample set is dropped for further processing, and processing returns in step 611 to step 605 of a next data sample set. If there are not less candidates than a predetermined number, then step 613 determines whether there are more candidate glints that a predetermined number. If there are more candidates, in step 615, the one or more processors select as glints the predetermined number of candidates which most closely fit the predetermined geometrical relationship between the glints. For example, for the rectangle, which candidates most closely form the rectangle of the predetermined size and shape. If there are not more candidates than the number, the number of candidates matches the predetermined number of glints, and the candidates are selected as the glints in step 617.

Due to the geometry of the placement of illuminators for generating the glints as discussed above, the glints appear in the same locations, barring movement of the frame 115 with respect to the eye. Furthermore, as the positioning of the illuminators with respect to each other on the support structure of the frame 115 or lens 118 is fixed, the spatial relationship of the glints to each other in the image is fixed as well. As for size, as the glints are very small, the number of pixels making up the glint area on the sensor and in the sensed image would be correspondingly small. For example, if the image sensor of the camera has a 1000 pixels, each glint may take up less than ten pixels. Glints may be monitored in each image frame taken for example at 30 or 60 frames a second and an area may be identified as a glint from a number of frame samples. There may not be glint data in every frame. Sampling accommodates or smoothes out obstructions of glint, and pupil data, in different image frames such as due to factors like an eyelid or eyelash covering the glint and/or pupil. An image frame is an example of an image format.

FIG. 9 is a flowchart of a method embodiment which may be used to implement step 602 of determining boundaries for a gaze detection coordinate system. One or more processors determines a position of a center 164 of a cornea of each eye with respect to the illuminators 153 and at least one light sensor, e.g. 134 or 152, based on glints in step 612. Based on image data provided by the at least one sensor, in step 614, the one or more processors determine a pupil center of each eye. In step 616, the position of the center of eyeball rotation, which may be treated as fixed, is determined relative to the cornea and pupil centers. For example, based on the pupil center, a ray can be extended back through the determined cornea center 164 to the fixed center 166 of eyeball rotation. Additionally, distance or length approximations are used for approximating the length on the optical axis between the pupil and the cornea, for example about 3 mm, and the length on the optical axis between the center of curvature of cornea and the center of eyeball rotation, about 6 mm. These values have been determined from population studies of human eye parameters such as those compiled by Gullstrand. (See Hennessey, p. 88).

Optionally, the one or more processors in step 618 determines a position of the fixed center of eyeball rotation with respect to the illuminators and the at least one sensor for the respective eye. This position determined in step 618 provides a depth distance between a fixed point, or one that can be approximated as fixed for accuracy considerations of gaze detection, and the display optical system. In effect, a depth axis has been defined for the gaze detection coordinate system. Changes detected along the depth axis may be used to indicate that the near-eye display system has moved and trigger determination of boundaries of the coordinate system again or re-calibration of training gaze data sets as discussed below.

FIG. 10 illustrates a method embodiment for determining a position of the center of the cornea in the coordinate system with optical elements of the see-through, near-eye, mixed reality display. The one or more processors generate in step 622 a first plane including points including positions of a first illuminator for generating a first glint, a pupil center of the at least one image sensor, e.g. camera entrance pupil center, and the first glint. As in the embodiment of FIG. 3A, the pupil center of the camera may be positioned in relation to the detection area 139 which acts as an image plane and which directs the light it receives to an image sensor in another location. In other examples, like in FIGS. 3B and 3C, the detection area 139 may be the image sensor itself which is the image plane. This first plane will also include a position of the cornea center. Similarly, the one or more processors generate in step 624 a second plane including points including positions of a second illuminator for generating a second glint, the same pupil center of at least one sensor and the second glint. The two planes share the same camera pupil center as an origin and a distance vector to each illuminator is fixed with respect to the camera pupil center as the image sensor and illuminators are positioned on the near-eye display device at predetermined locations. These predetermined locations allow the various points in the planes to be related to each other in a third coordinate system including the two illuminators, the position of the camera pupil center, and the cornea center of curvature. The processor determines in step 626 the position of the cornea center of curvature based on the intersection of the first and second planes.

Figure 11:
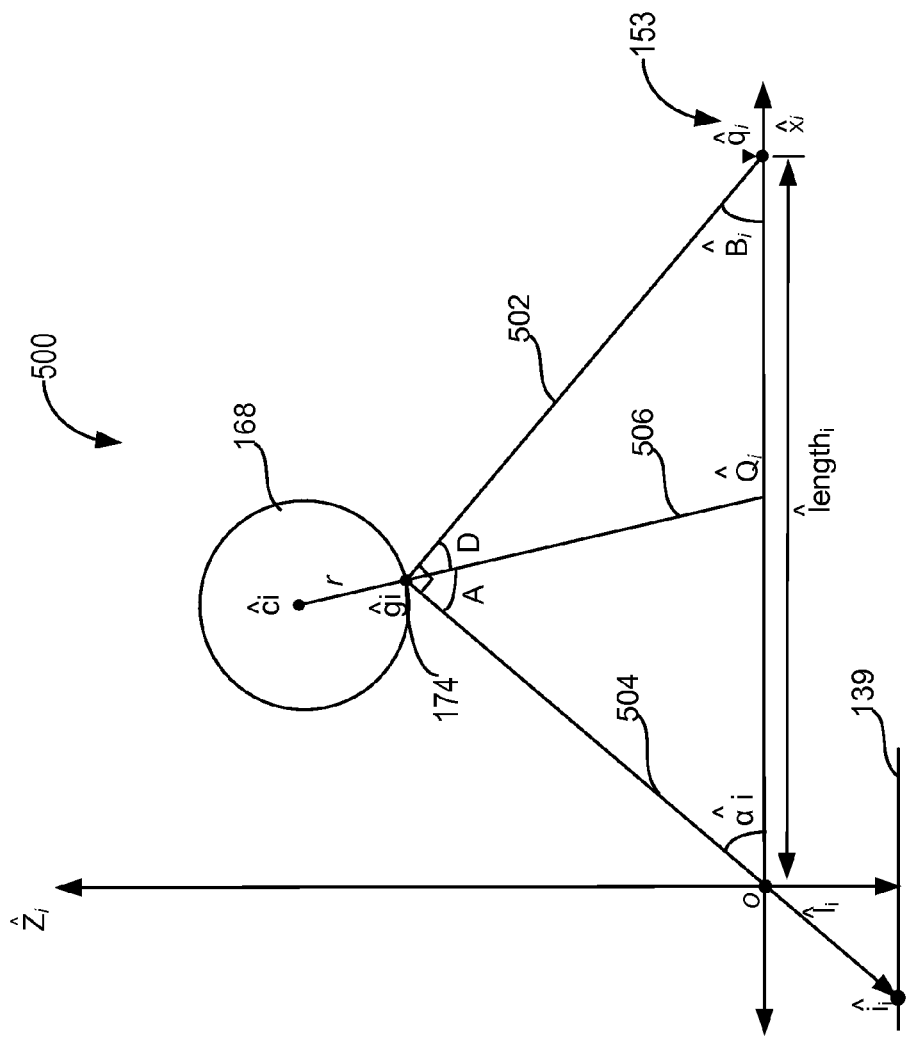
FIG. 11 provides an illustrative example of defining a plane using the geometry provided by the arrangement of optical elements to form the gaze detection coordinate system which may be used by the embodiment of FIG. 10 to find the cornea center.

FIG. 11 provides an illustrative example of the geometry of a gaze detection coordinate system 500 which may be used by the embodiment of FIG. 10 to find the cornea center. In this embodiment, the at least one sensor is a camera modeled as a pin-hole camera. The geometry depicted is a slightly modified version of FIG. 3 on page 89 of Hennessey et al. "A Single Camera Eye-Gaze Tracking System with Free Head Motion," ETRA 2006, San Diego, Calif., ACM p. 88, pp. 87-94 (hereafter Hennessey), which is hereby incorporated by reference. A list of variables is provided as follows:

$\hat{q}_i$ is a position of an illuminator$_i$, the light of which produces glint $\hat{g}_i$, (e.g. 174)

$\hat{g}_i$ is the glint produced by illuminator$_i$ (153) on a cornea surface, $\hat{o}$ is a camera pupil center of the pin-hole camera model, $\hat{i}_i$ is the image of glint $\hat{g}_i$ on the image plane which is the detection area 139 of the camera sensor, length$_i$ is the scalar distance or length from point $\hat{o}$ to $\hat{q}_i$, $\hat{I}_i$ is the vector from the camera pupil center $\hat{o}$ to the image $\hat{i}_i$ on the image sensor of the glint $\hat{g}_i$, $\hat{Q}_i$ is the vector from the camera pupil center $\hat{o}$ to the position $\hat{q}_i$ of illuminator$_i$, the $\hat{X}_i$ axis is defined along $\hat{Q}_i$, in this example and the $\hat{Z}_i$ axis of the coordinate system is such so that $\hat{I}_i$ which connects the image $\hat{i}_i$ of the glint $\hat{g}_i$ on image plane 139 (detection area) lies in a plane formed by the $\hat{X}_i$ and $\hat{Z}_i$ axes.

$\hat{\beta}$ is an angle formed in the $\hat{X}_i\hat{Z}_i$ plane between a line 502 representing the incident ray of light from the illuminator (153) position $\hat{q}_i$ to the glint $\hat{g}_i$ (174) on a cornea surface.

$\hat{\alpha}$ is the angle formed in the $\hat{X}_i\hat{Z}_i$ plane between a line 504 representing the reflected ray from the glint $\hat{g}_i$ to the camera pupil center of the camera, ô, which is also the origin of the coordinate system.

ĉ is the position of the cornea center which also lies in the $\hat{X}_i\hat{Z}_i$ plane.

As the cornea is modeled as a sphere, r is the radius of the corneal sphere, and each glint $\hat{g}_i$ is a point on the first or external surface of the sphere, so each glint is separated from the cornea center by the radius r. In the above example, the glint $\hat{g}_i$ is modeled as a point on the exterior surface or first surface of the cornea. In such a model, the light of the illuminator is bouncing off the cornea in the same medium, air, of the same index of refraction as the reflected light of the glint directed back to the camera sensor.

As shown in FIG. 11, a line or ray 506 normal to the glint $\hat{g}_i$ on the surface of the cornea can be extended from the glint in the direction of the cornea and also extended to intersect with the $\hat{X}_i$ axis of the $\hat{X}_i\hat{Z}_i$ plane of the coordinate system. Also as shown in FIG. 11, the incident ray 502 and the reflected ray 504 make a right triangle with the line length $l_i$ between the position of the illuminator $\hat{q}_i$ and the camera pupil center ô. Thus angle A and angle D is each represented by $$\frac{\pi - \hat{\alpha}_i - \hat{\beta}_i}{2}$$

wherein $$\hat{\alpha}_i = \cos^{-1}\left(\frac{-\hat{l}_i \cdot \hat{Q}_i}{\|-\hat{l}_i\| \cdot \|\hat{Q}_i\|}\right) \text{ and } \hat{\beta}_i = \tan^{-1}\left(\frac{\hat{g}_{ix} \cdot \tan(\hat{\alpha}_i)}{\hat{l}_i - \hat{g}_{ix}}\right).$$

According to Hennessey, the center of the cornea $\hat{c}_i$ can be defined in the coordinate system 500 in terms of the unknown parameter $\hat{g}_{ix}$ resulting in 3 equations for 4 unknowns ($\hat{c}_{ix}$, $\hat{c}_{iy}$, $\hat{c}_{iz}$, $\hat{g}_{ix}$) as follows:

$$\begin{bmatrix}\hat{c}_{ix}\\\hat{c}_{iy}\\\hat{c}_{iz}\end{bmatrix} = \begin{bmatrix}\hat{g}_{ix} - r\cdot\sin\left(\frac{\hat{\alpha}_i - \hat{\beta}_i}{2}\right)\\0\\\hat{g}_{ix}\cdot\tan(\hat{\alpha}_i) + r\cdot\cos\left(\frac{\hat{\alpha}_i - \hat{\beta}_i}{2}\right)\end{bmatrix}$$

Another two-dimensional plane including the cornea center, ĉ, another glint $\hat{g}_i$, the camera pupil center ô of the camera and a position $\hat{q}_i$ of another illuminator is also formed. The camera pupil center ô of the camera and the cornea center are the same in each plane although the camera pupil center ô position is known. This will result in 6 equations with 8 unknowns. In Hennessey, the gaze detection coordinate system is treated as an auxiliary coordinate system for which a rotation matrix $\hat{R}_i$ can transform points between the auxiliary coordinate systems for each plane and a single world coordinate system such as the third coordinate system which relates the position of the detection area 139 to the illuminators 153. A constraint exists in which the cornea center defined for each glint is the same in the world coordinate system, e.g. $\hat{c}_1 = \hat{c}_2$ and 3 equations result for the different axis components, e.g., $\hat{c}_{1x} = \hat{c}_{2x}$, $\hat{c}_{1y} = \hat{c}_{2y}$, and $\hat{c}_{1z} = \hat{c}_{2x}$, thus providing 9 equations with 8 unknowns. Hennessey (p. 90) states to solve numerically for ĉ using a gradient descent algorithm. Thus, the position center 164 of the cornea 168 is defined with respect to the positions of the illuminators and the image plane or detection area 139.

Figures 12, 13:
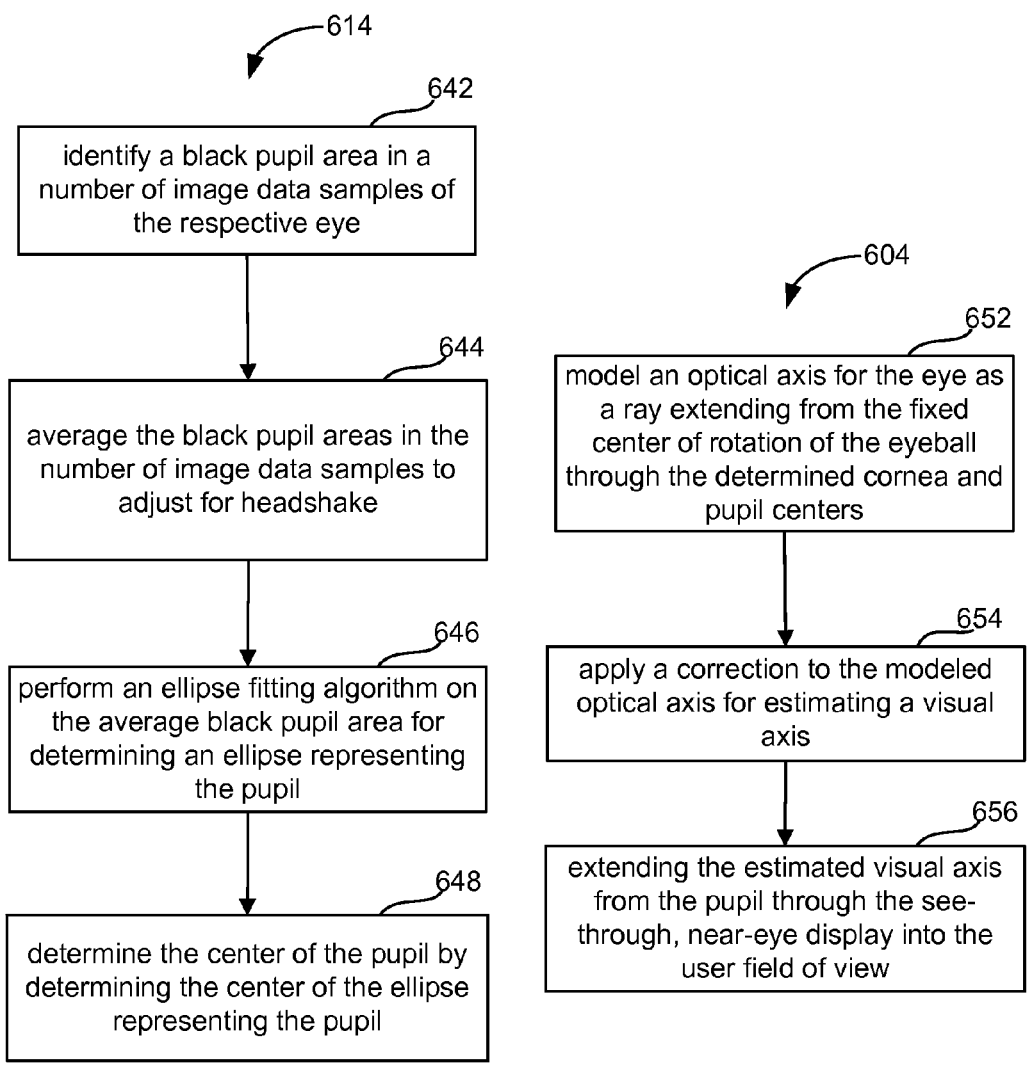
FIG. 12 is a flowchart illustrating a method embodiment for determining a pupil center from image data generated by a sensor.
FIG. 13 is a flowchart illustrating a method embodiment for determining a gaze vector based on the determined centers for the pupil, the cornea and a center of rotation of an eyeball.

FIG. 12 illustrates a method embodiment for determining a pupil center from image data generated by a sensor. In step 642, the one or more processors identify a black pupil area in a number of image data samples of the respective eye and in step 644 averages the black pupil areas in the number of image data samples to adjust for headshake. An assumption may be made that a pupil is a circle and when viewed from an angle is an ellipse. One axis of the ellipse, the major axis, remains constant as it represents the diameter of the pupil which does not change, provided the lighting does not change, as pupil size changes with lighting changes.

The pupil appears as a circle in an image format such as an image frame of a camera having its detection area centered on the optical axis of the display when the pupil is looking straight ahead through the display. As the pupil changes its gaze and moves from the center of the image frame, the pupil appears as an ellipse, as a circle viewed from an angle appears as an ellipse. The width of the minor axis of the ellipse changes with gaze changes. A narrow ellipse to the left of the center of the image frame indicates the user is looking to the far right. A wider ellipse a distance less to the right of the center of the image frame indicates the user is looking left but not far left.

The center of the pupil is the center of the ellipse. The ellipse is fitted from detected edge points in the image. Because such edge points are noisy and not all of them are on the ellipse, the ellipse fitting process is repeated many times over randomly selected subsets of all edge points. The subset that is most consistent with all the edge points is used to obtain the final ellipse. The processor in step 646 performs an ellipse fitting algorithm on the average black pupil area for determining an ellipse representing the pupil, and in step 648 determines the center of the pupil by determining the center of the ellipse representing the pupil.

With the center of rotation, the cornea center and the pupil center identified, one can extend a ray from the center of rotation through the cornea and pupil centers to obtain an optical axis for the eye. However, as noted previously, a gaze vector in a human is the visual axis or line of sight from the fovea through the pupil center. Photoreceptors in the fovea region of the human retina are more densely packed than in the rest of the retina. This area provides the highest visual acuity or clearness of vision, and also provides stereoscopic vision of nearby objects. After determining the optical axis, a default offset angle may be applied so that the optical axis approximates the visual axis and is selected as the gaze vector.

FIG. 13 illustrates a method embodiment for determining a gaze vector based on the determined centers for the pupil, the cornea and the rotation of the eyeball and which embodiment may be used to implement step 604. In step 652, the one or more processors model an optical axis 178 for the eye as a ray extending from the fixed center of rotation of the eyeball through the determined cornea and pupil centers and in step 654 applies a correction to the modeled optical axis for estimating a visual axis. In step 656, the one or more processors extend the estimated visual axis from the pupil through the display optical system of the see-through, near-eye display into the user field of view.

In one embodiment, with the fixed positioning of the illuminators as a basis, the effect of different areas of the eye on reflectivity and hence on the amount or intensity of light reflected is used as a basis for gaze detection. Intensity data from either IR or visible light sensors may be used to determine gaze, so the reflectivity data may be based on IR based reflectivity or visible light reflectivity. For illustration, the sclera is more reflective than other areas of the eye like the pupil and the iris. If a user looks to the user's far left, an illuminator 153 located on the frame 115 at the user's far right causes a glint reflection on the right sclera of the user's right eye. PSD 134r or as in FIG. 3B, photodetector 152 on the inner right frame near bridge 104 receives more reflected light represented in a data reading while the light from reflection at the other photodector 152 or position on the PSD when the illuminator 153 nearest the bridge is turned on receives a lower amount of reflected light in a range associated with the black pupil. The reflectivity of the iris may also be captured by camera 134 and stored for the user by the processor 210, the processing unit 4 or a mobile device 5 embodying the processing unit 4.

The accuracy may not be as much as those based on images of the full eye, but may suffice for many applications. Additionally, such a gaze detection may be useful as an auxiliary or backup gaze detection technique. For example, during computationally intensive periods of generating complex virtual images, such a glint based technique relieves some processor overhead. Furthermore, such a glint-based technique can be executed many more times in a time period than an image based technique which processes more data or a computationally intensive but more accurate technique which may be run at a slower rate to recalibrate accuracy of gaze detection periodically. An example of a gaze detection technique which is both image based and more computationally intensive is one for determining a gaze vector with respect to inner parts of the eye based on glint data and pupil image data like the embodiments described in FIGS. 7 to 13 which may be run at a slower rate to recalibrate accuracy of gaze detection periodically. For example, an embodiment of the more computationally intensive technique based in part on image data may be run at ten (10) times a second while the glint based gaze detection technique may be run at a faster rate of one hundred (100) times per second or even five (500) hundred in some instances.

Figure 14:
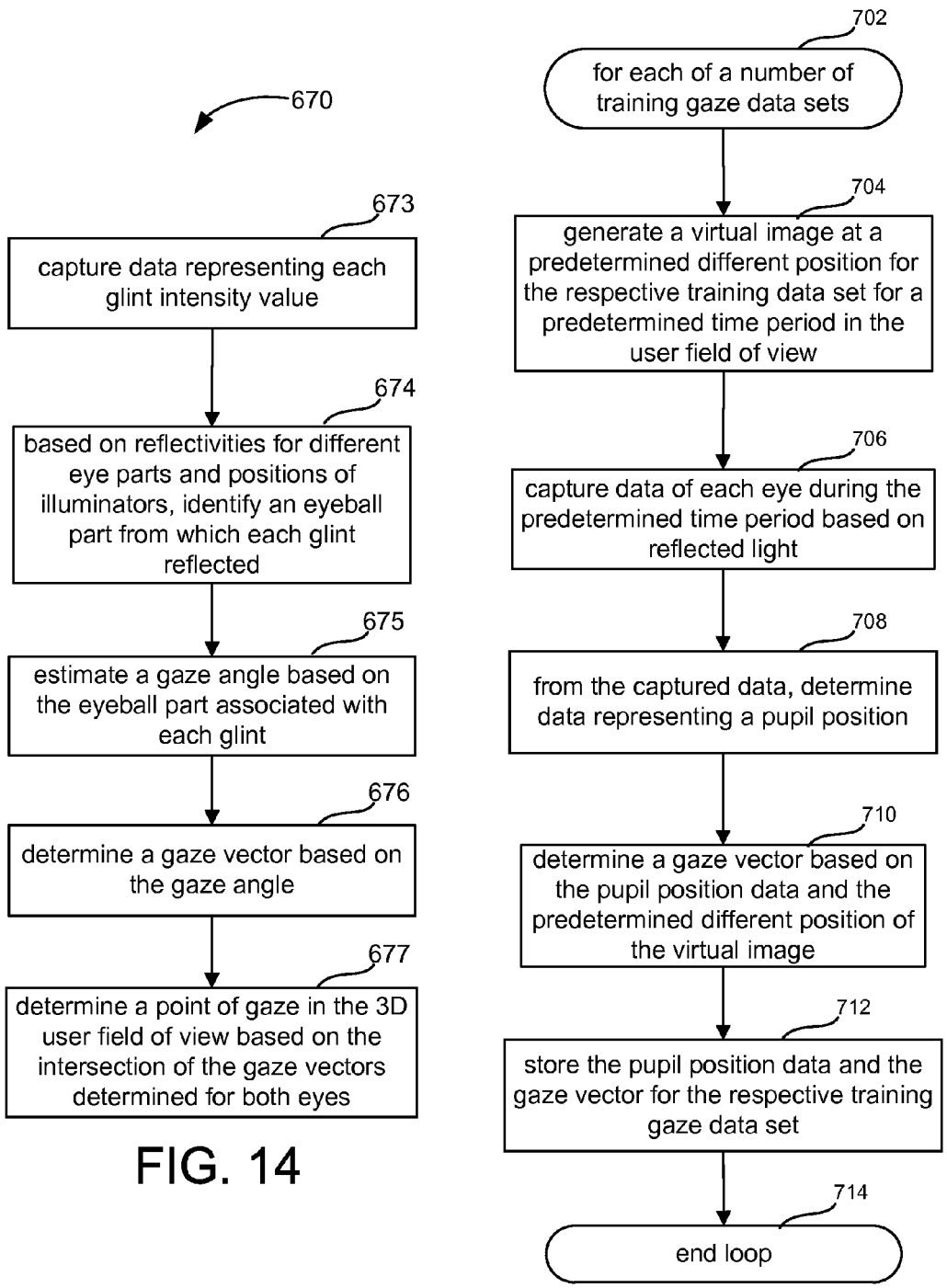
FIG. 14 is a flowchart illustrating a method embodiment for determining gaze based on glint data.

FIG. 14 is a flowchart illustrating a method embodiment for determining gaze based on glint data. In step 673, data is captured representing each glint intensity value. Based on specular reflectivities of different eye parts, and positions of illuminators, an eyeball part is identified in step 674 based on the intensity value detected for each glint position in a geometrical relationship of the glints. In step 675, a gaze angle is estimated based on the eyeball part associated with each of the glint positions. As described in previous examples, an eyeball part may be an iris, a pupil or a sclera of the eyeball. The positions of the illuminators form a geometry for the glints, e.g. a box, a circle, a rectangle, etc. which frame or surround the pupil, at least on two sides. A gaze vector is determined in step 676 based on the gaze angle, and a point of gaze in the 3D user field of view is determined in step 677 based on the intersection of the gaze vectors determined for both eyes.

As noted above, different methods with different accuracies may be employed at different periodic rates to trade accuracy for speed. A method embodiment based on glint intensity values such as that described in FIG. 14 is an example of a technique with a low computational intensity which may be employed. In another example, training gaze data sets may be used for comparison with current pupil position data to determine a gaze vector.

Using training data sets for gaze determination relies on the assumption that the near-eye display device 2 with respect to the eye has not moved. If movement is detected, the training gaze data sets are to be recalibrated. A lighting change may also be a basis for recalibration.

A training gaze data set is acquired for each of a set of predetermined gaze directions. For example, training data sets may be obtained for different sections of the display optical system 14 through which the user's pupils gaze at a gaze or pupil angle. In one example, there are nine (9), one for each of the four (4) corners of the display optical system, a middle left side block or area, a middle right side block or area, a top middle block, a bottom middle block, and a center area. In the case of glints, a comparison of intensity values at the four glint positions for current data against training data sets may be used.

Figure 15:
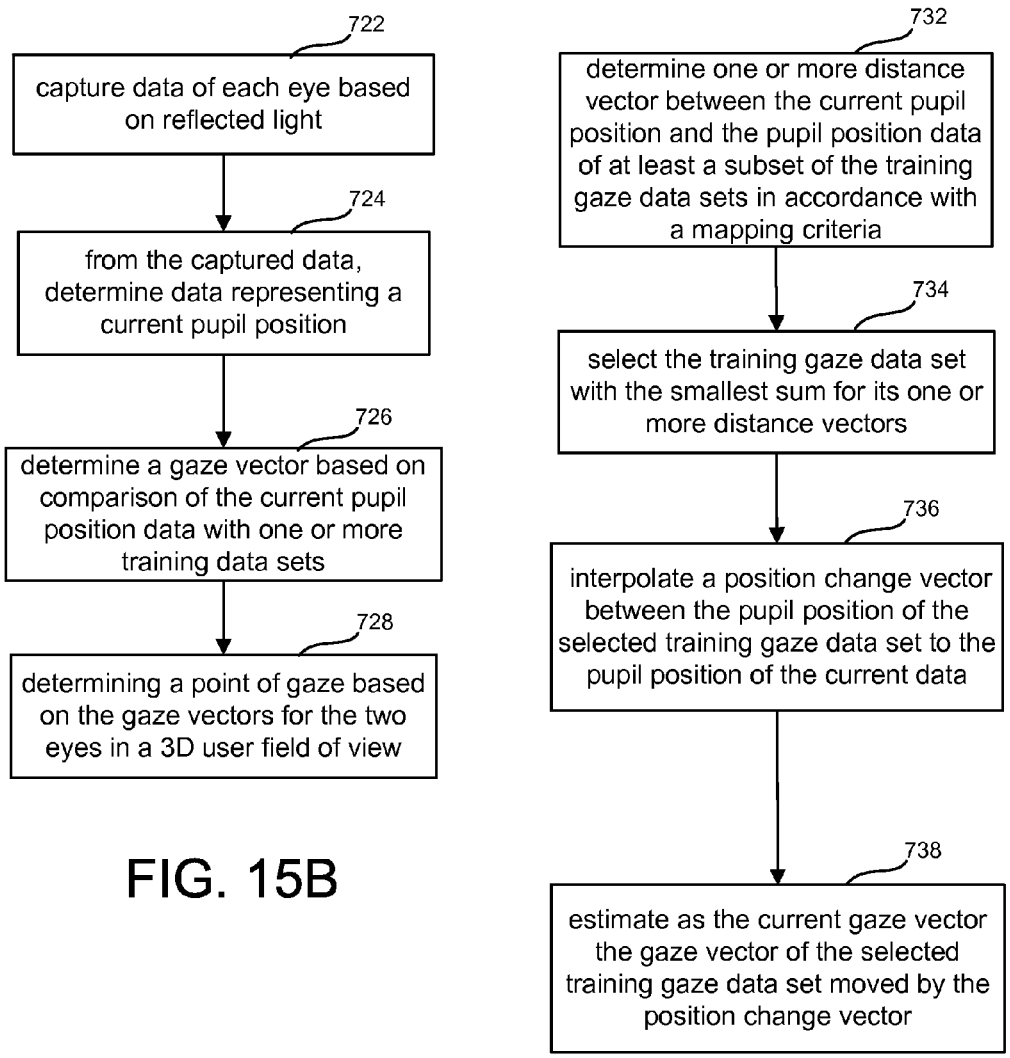
FIG. 15a is a flowchart illustrating a method embodiment for generating a set of training data sets for a comparison based determination of gaze.
FIG. 15b is a flowchart illustrating a method embodiment for determining gaze based on the training data sets.
FIG. 15c is a flowchart of an interpolation method embodiment which may be used with the comparison step of FIG. 14.

FIG. 15a is a flowchart illustrating a method embodiment for generating a set of training data sets for a comparison based determination of gaze. The method may be used to determine training sets for gaze angles based glint intensity value data representing pupil positions. The method embodiment is presented in an exemplar loop structure beginning at step 702 and ending at step 714. For each of a number of training gaze data sets, one or more processors of the control circuitry 136, the processing unit 4, the mobile device 5, a networked hub computing environment 12 alone or in combination, generate in step 704 a virtual image at a predetermined different position for the respective training data set for a predetermined time period in the user field of view. As previously discussed, the microdisplay 120 generates virtual images at different positions in the user field of view.

In step 706, data of each eye is captured during the predetermined time period based on glints. In step 708 from the captured data, the one or more processors determine data representing a pupil position, for example, a set of intensity values from a number of glints. In step 710, a gaze vector is determined based on the pupil position data and the predetermined different position of the virtual image in the user field of view. In the case of pupil and glint data being captured, a gaze vector may be determined based on the cornea center, pupil center and fixed center of eyeball rotation as discussed above with respect to the embodiments of FIGS. 7 to 13 and the position of the virtual image as a check. In the case of glint only data, the intensity values of the glints may be correlated with stored values reflecting different areas of reflection on the eye and is associated with a gaze vector extending to the virtual image position in the user field of view. The glint values may be checked against a set of values for the expected angle of the pupil viewing the virtual image at the predetermined position. In step 712, the one or more processors store the pupil position data and the gaze vector for the respective training gaze data set and proceeds in steps 714 and 702 to start processing the next training gaze data set until the predetermined number of sets is reached.

FIG. 15B is a flowchart illustrating a method embodiment for determining gaze based on the training data sets. In step 722, the at least one sensor captures data of each eye based on reflected light and the one or more processors determine from the captured data in step 724 data representing a current pupil position. In step 726, the one or more processors determine a gaze vector based on comparison of the current pupil position data with one or more training data sets and determines in step 728 a point of gaze based on the gaze vectors for the two eyes, e.g. where the two vectors intersect in a 3D user field of view.

FIG. 15C is a flowchart of an interpolation method embodiment which may be used with the comparison step 726 of FIG. 15B. For example, this embodiment may be used when comparing sensor data of the spatial relationship between the glints, for example, PSD data. In step 732, the one or more processors determine one or more distance vectors between the current pupil position data and the pupil position data of at least a subset of the training gaze data sets in accordance with a mapping criteria. On the detection area of a sensor, for example a camera sensor or discrete position sensitive detector, the mapping may be a distance in mm to pixel mapping. For an isotropic PSD, the mapping may be an area on the detector area to a distance in mm.

The box or other geometric shape of glints provides another example. A distance vector for each current glint from a training gaze data set of glint intensity values indicates a direction of intensity change as the glints are fixed barring movement of the coordinate system.

In step 734, the one or more processors select the training gaze data set with the smallest sum for its one or more distance vectors and in step 736 interpolates a position change vector between the pupil position of the selected training gaze data set to the pupil position of the current data. In step 738, the one or more processors estimate as the current gaze vector the gaze vector of the selected training gaze data set moved by the position change vector Particularly when using training data for comparison, movement of the gaze detection coordinate system is a cause for recalibrating the training data sets. One may periodically redetermine the positions of the cornea center and fixed center of rotation to determine whether there has been a change in the spatial relationship between them and the illuminators and at least one sensor.

Other tests for movement may be performed based on a facial feature with a fixed characteristic in image data. In one embodiment, an eye camera may capture about 5 to 10 mm of area around the visible eyeball portion of the cornea bulge, eye white, iris and pupil so as to capture part of an eyelid and eyelashes. A positionally fixed facial feature like a mole or freckle on skin such as an eyelid or on the bottom rim of the skin encasing the lower eyeball may also be present in the image data of the eye. In image samples, the position of the mole or freckle may be monitored for a change in position. If the facial feature has moved up, down, right or left, a vertical or horizontal shift can be detected. If the facial feature appears larger or smaller, a depth change in the spatial relationship between eye and display device 2 can be determined. There may be a criteria range in the change of position to trigger recalibration of the training gaze data sets due to things like camera resolution, etc.

In another example, although lighting is a factor which changes the size of the pupil and the ratio of pupil area to visible iris area within the circumference or perimeter of the iris, the size of the perimeter or circumference of the iris does not change with gaze change or lighting change; hence, the perimeter or circumference is a fixed characteristic of the iris as a facial feature. Through ellipse fitting of the iris, the one or more processors can determine whether the iris has become larger or smaller in image data in accordance with criteria. If larger, the display device 2 with its illuminators 153 and at least one sensor 134 has moved closer in depth to the user's eye; if smaller, the display device 2 has moved farther away. A change in a fixed characteristic can trigger a recalibration of training data sets.

Figure 16:
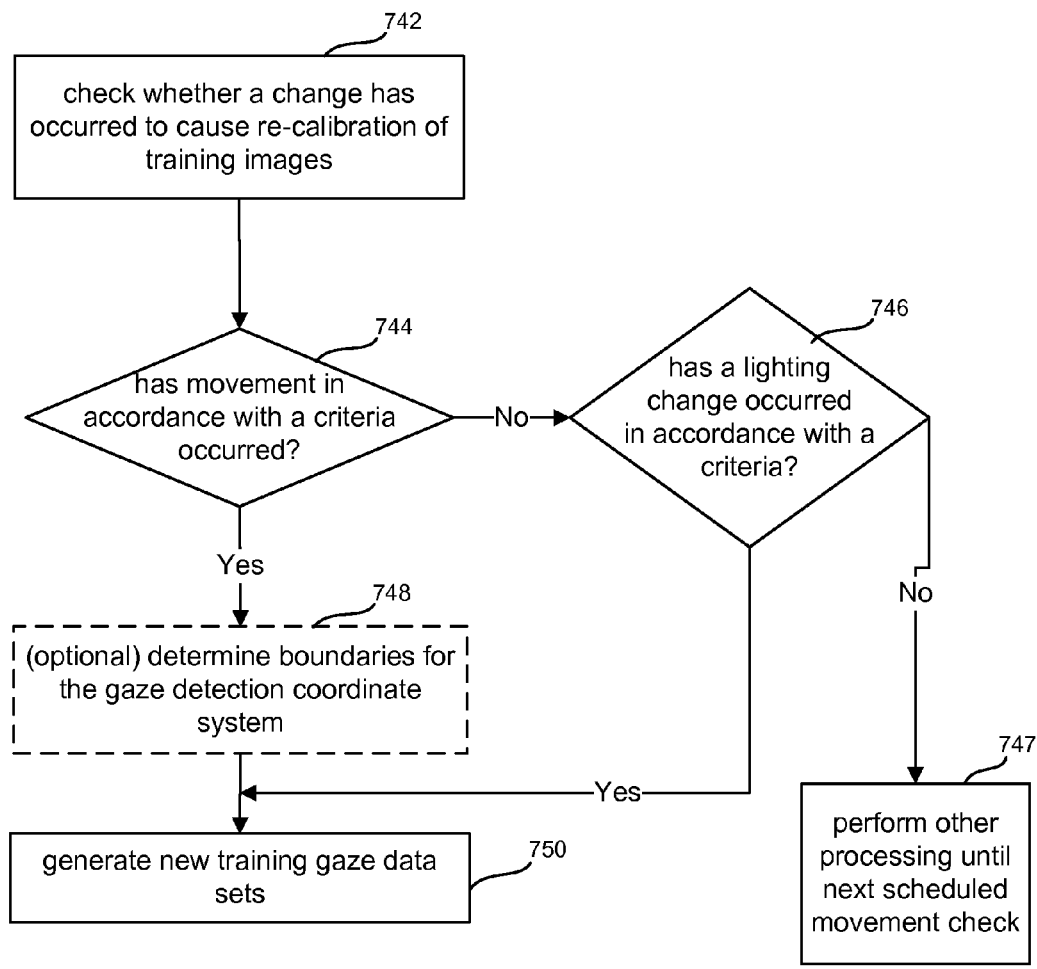
FIG. 16 is a flowchart illustrating a method embodiment for checking whether re-calibration of a training gaze data sets is to be done.

FIG. 16 is a flowchart illustrating a method embodiment for checking calibration of a gaze determination system. The one or more processors of or in communication with the display device 2 in step 742 check whether a change has occurred to cause re-calibration of training data sets. One of the checks is determining in step 744 whether movement in accordance with a criteria has occurred. The check may be periodically determining a gaze vector in three dimensions as discussed per FIGS. 7 through 13 and noting the position of the fixed eyeball rotation has changed with respect to one or more gaze detection elements on the see-through, near-eye display device. The criteria may be a distance of movement in any of three dimensions. Based on the result of the determination in step 744 of has movement occurred indicating no movement, the one or more processors determine in step 746 whether a lighting change in accordance with a criteria has occurred. Responsive to a negative determination in step 746, other processing until next scheduled movement check is performed in step 747. If movement was indicated, the movement may have been detected in a image based technique based on a facial feature. Therefore, an optional step 748 may be performed of determining the boundaries for the gaze detection coordinate system as discussed for the embodiments of FIGS. 7 through 13. Responsive to the movement, a new set of training gaze data sets is generated in step 750. Furthermore, if it was determined in step 746, that there was a lighting change which exceeds a threshold or other criteria, the new set of training gazed data sets may also be triggered in step 750.

Figure 17:
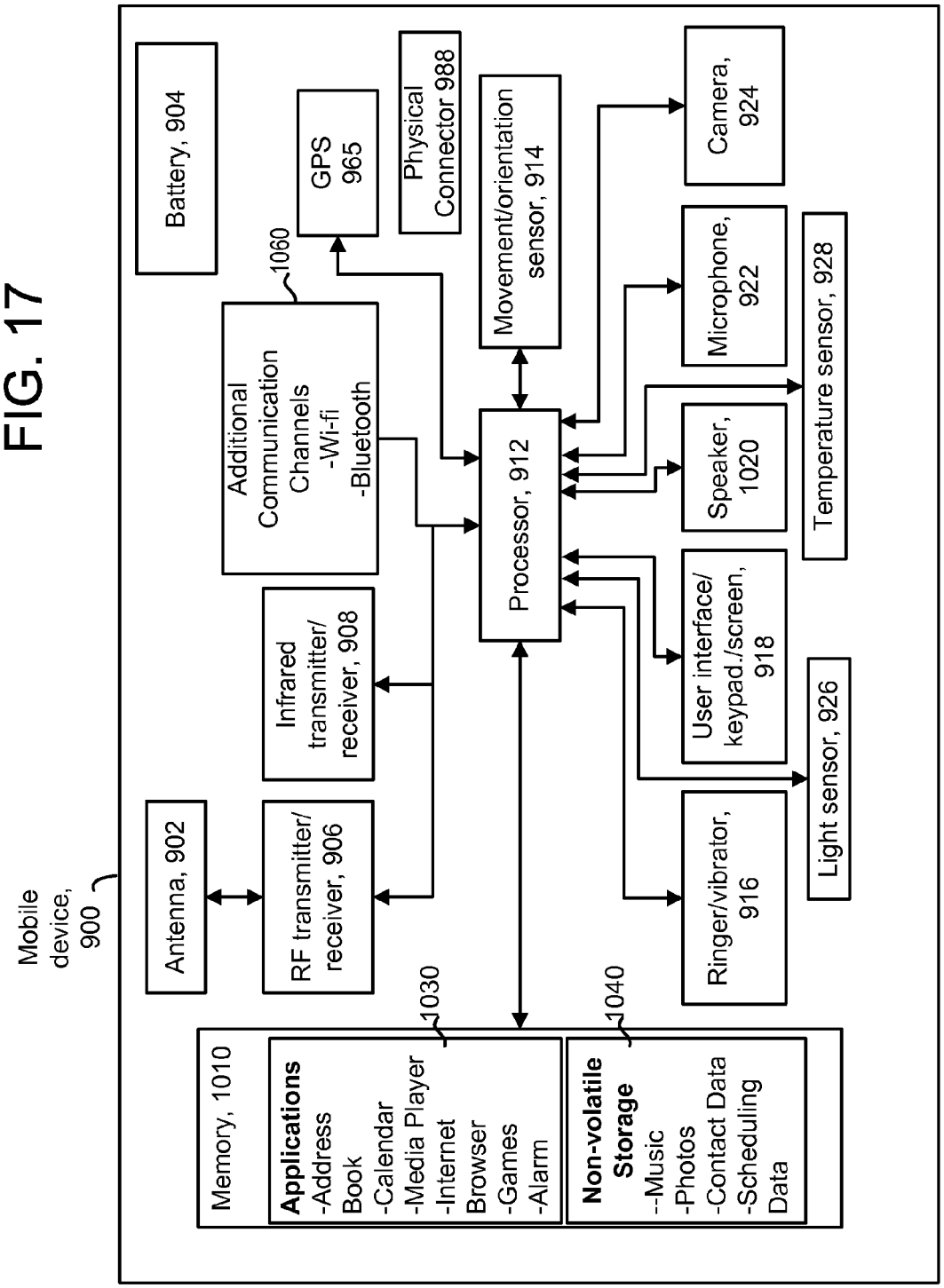
FIG. 17 is a block diagram of an exemplary mobile device which may operate in embodiments of the technology.

FIG. 17 is a block diagram of an exemplary mobile device which may operate in embodiments of the technology. Exemplary electronic circuitry of a typical mobile phone is depicted. The phone 900 includes one or more microprocessors 912, and memory 1010 (e.g., non-volatile memory such as ROM and volatile memory such as RAM) which stores processor-readable code which is executed by one or more processors of the control processor 912 to implement the functionality described herein.

Mobile device 900 may include, for example, processors 912, memory 1010 including applications and non-volatile storage. The processor 912 can implement communications, as well as any number of applications, including the interaction applications discussed herein. Memory 1010 can be any variety of memory storage media types, including non-volatile and volatile memory. A device operating system handles the different operations of the mobile device 900 and may contain user interfaces for operations, such as placing and receiving phone calls, text messaging, checking voicemail, and the like. The applications 1030 can be any assortment of programs, such as a camera application for photos and/or videos, an address book, a calendar application, a media player, an internet browser, games, other multimedia applications, an alarm application, other third party applications, the interaction application discussed herein, and the like. The non-volatile storage component 1040 in memory 1010 contains data such as web caches, music, photos, contact data, scheduling data, and other files.

The processor 912 also communicates with RF transmit/receive circuitry 906 which in turn is coupled to an antenna 902, with an infrared transmitted/receiver 908, with any additional communication channels 1060 like Wi-Fi or Bluetooth, and with a movement/orientation sensor 914 such as an accelerometer. Accelerometers have been incorporated into mobile devices to enable such applications as intelligent user interfaces that let users input commands through gestures, indoor GPS functionality which calculates the movement and direction of the device after contact is broken with a GPS satellite, and to detect the orientation of the device and automatically change the display from portrait to landscape when the phone is rotated. An accelerometer can be provided, e.g., by a micro-electromechanical system (MEMS) which is a tiny mechanical device (of micrometer dimensions) built onto a semiconductor chip. Acceleration direction, as well as orientation, vibration and shock can be sensed. The processor 912 further communicates with a ringer/vibrator 916, a user interface keypad/screen, biometric sensor system 918, a speaker 1020, a microphone 922, a camera 924, a light sensor 926 and a temperature sensor 928.

The processor 912 controls transmission and reception of wireless signals. During a transmission mode, the processor 912 provides a voice signal from microphone 922, or other data signal, to the RF transmit/receive circuitry 906. The transmit/receive circuitry 906 transmits the signal to a remote station (e.g., a fixed station, operator, other cellular phones, etc.) for communication through the antenna 902. The ringer/vibrator 916 is used to signal an incoming call, text message, calendar reminder, alarm clock reminder, or other notification to the user. During a receiving mode, the transmit/receive circuitry 906 receives a voice or other data signal from a remote station through the antenna 902. A received voice signal is provided to the speaker 1020 while other received data signals are also processed appropriately.

Additionally, a physical connector 988 can be used to connect the mobile device 900 to an external power source, such as an AC adapter or powered docking station. The physical connector 988 can also be used as a data connection to a computing device. The data connection allows for operations such as synchronizing mobile device data with the computing data on another device.

A GPS transceiver 965 utilizing satellite-based radio navigation to relay the position of the user applications is enabled for such service.

The example computer systems illustrated in the figures include examples of computer readable storage media. Computer readable storage media are also processor readable storage media. Such media may include volatile and nonvolatile, removable and non-removable media implemented in any method or technology for storage of information such as computer readable instructions, data structures, program modules or other data. Computer storage media includes, but is not limited to, RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other medium which can be used to store the desired information and which can accessed by a computer.

Figure 18:
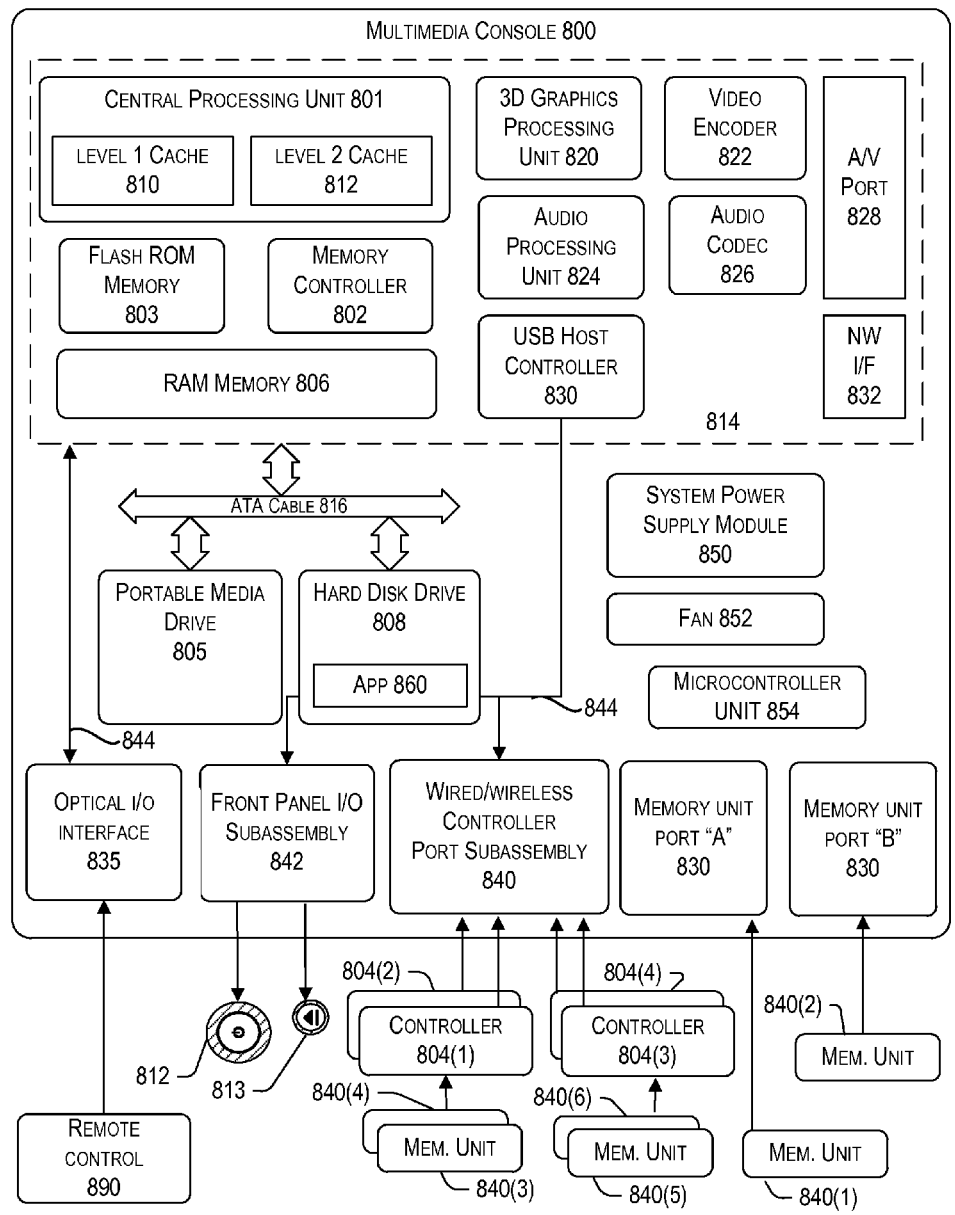
FIG. 18 is a block diagram of one embodiment of a computing system that can be used to implement a hub computing system.

FIG. 18 is a block diagram of one embodiment of a computing system that can be used to implement the hub computing system of FIGS. 1A and 1B. In this embodiment, the computing system is a multimedia console 800, such as a gaming console. As shown in FIG. 18, the multimedia console 800 has a central processing unit (CPU) 801, and a memory controller 802 that facilitates processor access to various types of memory, including a flash Read Only Memory (ROM) 803, a Random Access Memory (RAM) 806, a hard disk drive 808, and portable media drive 806. In one implementation, CPU 801 includes a level 1 cache 810 and a level 2 cache 812, to temporarily store data and hence reduce the number of memory access cycles made to the hard drive 808, thereby improving processing speed and throughput.

CPU 801, memory controller 802, and various memory devices are interconnected via one or more buses (not shown). The details of the bus that is used in this implementation are not particularly relevant to understanding the subject matter of interest being discussed herein. However, it will be understood that such a bus might include one or more of serial and parallel buses, a memory bus, a peripheral bus, and a processor or local bus, using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus.

In one implementation, CPU 801, memory controller 802, ROM 803, and RAM 806 are integrated onto a common module 814. In this implementation, ROM 803 is configured as a flash ROM that is connected to memory controller 802 via a PCI bus and a ROM bus (neither of which are shown). RAM 806 is configured as multiple Double Data Rate Synchronous Dynamic RAM (DDR SDRAM) modules that are independently controlled by memory controller 802 via separate buses (not shown). Hard disk drive 808 and portable media drive 805 are shown connected to the memory controller 802 via the PCI bus and an AT Attachment (ATA) bus 816. However, in other implementations, dedicated data bus structures of different types can also be applied in the alternative.

A graphics processing unit 820 and a video encoder 822 form a video processing pipeline for high speed and high resolution (e.g., High Definition) graphics processing. Data are carried from graphics processing unit (GPU) 820 to video encoder 822 via a digital video bus (not shown). Lightweight messages generated by the system applications (e.g., pop ups) are displayed by using a GPU 820 interrupt to schedule code to render popup into an overlay. The amount of memory used for an overlay depends on the overlay area size and the overlay preferably scales with screen resolution. Where a full user interface is used by the concurrent system application, it is preferable to use a resolution independent of application resolution. A scaler may be used to set this resolution such that the need to change frequency and cause a TV resync is eliminated.

An audio processing unit 824 and an audio codec (coder/decoder) 826 form a corresponding audio processing pipeline for multi-channel audio processing of various digital audio formats. Audio data are carried between audio processing unit 824 and audio codec 826 via a communication link (not shown). The video and audio processing pipelines output data to an A/V (audio/video) port 828 for transmission to a television or other display. In the illustrated implementation, video and audio processing components 820-828 are mounted on module 214.

FIG. 18 shows module 814 including a USB host controller 830 and a network interface 832. USB host controller 830 is shown in communication with CPU 801 and memory controller 802 via a bus (e.g., PCI bus) and serves as host for peripheral controllers 804(1)-804(4). Network interface 832 provides access to a network (e.g., Internet, home network, etc.) and may be any of a wide variety of various wire or wireless interface components including an Ethernet card, a modem, a wireless access card, a Bluetooth module, a cable modem, and the like.

In the implementation depicted in FIG. 18 console 800 includes a controller support subassembly 840 for supporting four controllers 804(1)-804(4). The controller support subassembly 840 includes any hardware and software components needed to support wired and wireless operation with an external control device, such as for example, a media and game controller. A front panel I/O subassembly 842 supports the multiple functionalities of power button 812, the eject button 813, as well as any LEDs (light emitting diodes) or other indicators exposed on the outer surface of console 802. Subassemblies 840 and 842 are in communication with module 814 via one or more cable assemblies 844. In other implementations, console 800 can include additional controller subassemblies. The illustrated implementation also shows an optical I/O interface 835 that is configured to send and receive signals that can be communicated to module 814.

MUs 840(1) and 840(2) are illustrated as being connectable to MU ports "A" 830(1) and "B" 830(2) respectively. Additional MUs (e.g., MUs 840(3)-840(6)) are illustrated as being connectable to controllers 804(1) and 804(3), i.e., two MUs for each controller. Controllers 804(2) and 804(4) can also be configured to receive MUs (not shown). Each MU 840 offers additional storage on which games, game parameters, and other data may be stored. In some implementations, the other data can include any of a digital game component, an executable gaming application, an instruction set for expanding a gaming application, and a media file. When inserted into console 800 or a controller, MU 840 can be accessed by memory controller 802. A system power supply module 850 provides power to the components of gaming system 800. A fan 852 cools the circuitry within console 800. A microcontroller unit 854 is also provided.

An application 860 comprising machine instructions is stored on hard disk drive 808. When console 800 is powered on, various portions of application 860 are loaded into RAM 806, and/or caches 810 and 812, for execution on CPU 801, wherein application 860 is one such example. Various applications can be stored on hard disk drive 808 for execution on CPU 801.

Gaming and media system 800 may be operated as a standalone system by simply connecting the system to monitor 16 (FIG. 1A), a television, a video projector, or other display device. In this standalone mode, gaming and media system 800 enables one or more players to play games, or enjoy digital media, e.g., by watching movies, or listening to music. However, with the integration of broadband connectivity made available through network interface 832, gaming and media system 800 may further be operated as a participant in a larger network gaming community.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A gaze vector determination system for use in a mixed reality display system comprising:
   at least one image generation unit for generating at least one virtual image for display by a near-eye, mixed reality display device;
   a respective arrangement of gaze detection elements positioned on the display device for forming a spatial relationship between the gaze detection elements and at least one eye, the gaze detection elements including:
   a set of illuminators for generating glints on the at least one eye each illuminator positioned on the display device at a respective predetermined position and generating illumination about a predetermined wavelength, and
   at least one sensor for capturing light reflected from the at least one eye and generating data representing the captured reflected light, the at least one sensor positioned at a predetermined position in relation to predetermined positions of the set of illuminators on the display device;
   a memory for storing software and the data; and
   one or more processors communicatively coupled to the at least one sensor to receive the data representing the captured reflected light and having access to the memory for storing the data, the one or more processors determining a gaze vector for the at least one eye based on the data representing the captured reflected light, wherein data representing the captured reflected light includes glint intensity data and wherein for the at least one eye, the one or more processors determining the gaze vector comprises:
   in a time period, using a first technique that comprises determining at least one of a center of a cornea and a center of a pupil based on image data of the at least one eye a first number of times, and
   during the same time period, using a second different technique based on the glint intensity data independent of the image data of the at least one eye for a second number of times.

2. The system of claim 1 wherein the one or more processors determining the gaze vector using the second different technique further comprises the one or more processors determining a position for each glint with respect to at least one eyeball part based on the glint intensity data and the predetermined positions of the set of illuminators and the at least one respective sensor.

3. The system of claim 2 wherein the values of the glint intensity data are correlated with stored values for specular reflectivities of different eye parts.

4. The system of claim 3 wherein the different eye parts comprise an iris or a pupil or a sclera or a combination of two or more of the iris, the pupil and the sclera.

5. The system of claim 1 further comprising:
   wherein the illuminators are infra-red (IR) illuminators which transmit about a predetermined wavelength;
   at least one light sensor is an IR camera for generating image data of the glints and the pupil; and
   wherein the one or more processors determining the gaze vector using the first technique comprises the one or more processors determining the gaze vector including the center of the cornea and the center of the pupil based on the image data of glints and the pupil and the spatial relationship.

6. The system of claim 1 further comprising:
   the one or more processors determining boundaries of a three dimensional gaze detection coordinate system for the at least one eye based on the spatial relationship between the gaze detection elements positioned on the near-eye, mixed reality display device and positions of the glints detected on the at least one eye;
   the one or more processors being communicatively coupled to the at least one image generation unit for displaying the at least one virtual image at different locations in a user field of view viewable in the display device;
   the one or more processors generating a training gaze data set for each different location by capturing image data of the pupil of the at least one eye by the at least one sensor during display of the at least one virtual image at each of the different locations, identifying a black pupil area in the image data for each location, applying an ellipse fitting algorithm to the black pupil area for identifying pupil position data identifying a position of the eye within an eyeball for each location; and determining a gaze vector based on the pupil position data and the boundaries of the three dimensional gaze detection coordinate system;
   the one or more processors storing training gaze data sets, each training gaze data set storing the pupil position data and the gaze vector determined during display of the virtual image at a respective location of the different locations; and wherein using a first technique that comprises determining at least one of a center of a cornea and a center of a pupil based on image data of the at least one eye a first number of times further comprises:

based on image data of the pupil in the data representing the captured reflected light, the one or more processors determining current pupil position data for the at least one eye, and the one or more processors determining the gaze vector based on comparison of the current pupil position data with pupil position data stored in the training gaze data sets and their associated stored gaze vectors.

7. The system of claim 5 further comprising:

wherein the one or more processors determining the gaze vector using the first technique is performed at a first rate; and the one or more processors determining the gaze vector by the second different technique is performed at a second rate faster than the first rate.

8. The system of claim 5 wherein the IR camera is aligned with an optical axis of a respective display optical system positioned by the display device to be seen through by a respective eye.

9. A method for determining a gaze vector of a user eye based on a gaze detection coordinate system of a near-eye display device comprising:

determining boundaries of the three dimensional gaze detection coordinate system based on positions of glints detected on the user eye, positions on the near-eye display device of illuminators for generating the glints and of at least one sensor for detecting the glints further comprising:

determining a position of a center of a cornea of the user eye with respect to the positions of the illuminators and the at least one sensor based on positions of glints detected on a cornea surface of the user eye, determining a position of the pupil center from image data generated from the at least one sensor further comprising:

identifying a black pixel area as a black pupil area in a number of image samples, averaging the black pupil areas to adjust for headshake, performing an ellipse fitting algorithm on the average black pupil area for determining an ellipse representing the pupil, and determining the center of the pupil by determining the center of the ellipse representing the pupil, and determining a position of a fixed center of eyeball rotation of the user eye based on the positions of the cornea center and the pupil center; and determining a gaze vector for the user eye based on the positions of the center of the cornea, the pupil center and fixed center of eyeball rotation.

10. The method of claim 9, wherein the coordinate system includes a depth axis and changes along the depth axis trigger redetermination of the boundaries.

11. The method of claim 9 wherein the coordinate system includes a depth axis and a change along the depth axis is determined based on a change of size of a facial feature in image data generated from the at least one sensor.

12. The method of claim 9 wherein the coordinate system includes a depth axis and changes along the depth axis trigger re-calibration of training data.

13. The method of claim 12, further comprising:

determining a position from the fixed center of eyeball rotation of the user eye with respect to the illuminators and the at least one sensor for determining movement of the display device with respect to the user eye.

14. The method of claim 9, wherein:

determining the position of the center of the cornea of the user eye with respect to the illuminators and at least one sensor based on positions of glints detected on a cornea surface of the user eye further comprises:

generating a first plane including points including a positions of a first illuminator which generates a first glint, a camera pupil center of a detection area of the at least one sensor, and the first glint on the cornea surface;

generating a second plane including points including a position of a second illuminator which generates a second glint, and the camera pupil center of the detection area of the at least one sensor, and the second glint; and determining the position of the cornea center based on the intersection of the first and the second planes.

15. The method of claim 14, wherein:

determining the position of the fixed center of eyeball rotation of the user eye based on the positions of the cornea center and the pupil center further comprises estimating the position of the fixed center of eyeball rotation of the user eye based on a vector from the position of the pupil center through the position of the cornea center having a length based on length approximations between the positions of the pupil center and the cornea center and between the positions of the cornea center and the center of eyeball rotation.

16. The method of claim 9, wherein:

determining a gaze vector for the user eye based on the positions of the center of the cornea, the pupil center and fixed center of eyeball rotation further comprises:

modeling an optical axis for the user eye as a ray extending from the fixed center of rotation of the eyeball through the cornea and pupil centers;

applying a correction to the modeled optical axis for estimating a visual axis; and extending the estimated visual axis from the pupil through a near-eye display supported by the near-eye display in front of the user eye into a user field of view.

17. A gaze vector determination system for use in a mixed reality display system comprising:

at least one image generation unit for generating at least one virtual image for display by a near-eye, mixed reality display device;

a set of infra-red illuminators for producing glints for a user eye, each illuminator having a predetermined position on the display device and generating infra-red radiation about a predetermined wavelength;

at least one sensor for detecting the glints reflected from the user eye and generating glint data including intensity data for the glints, the at least one sensor having a predetermined position in relation to one or more illuminator predetermined positions on the display device to detect infra-red reflected radiation about the predetermined wavelength;

a memory for storing software and data including glint data; and one or more processors communicatively coupled to the at least one sensor to receive the glint data and having access to the memory for storing the glint data, the one or more processors determining one or more glint positions relative to an eye part based on the glint intensity data, the predetermined position of each illuminator in the set of infra-red illuminators, and the at least one predetermined position of the at least one sensor for detecting the glints reflected from the user eye; and the one or more processors determining a gaze vector for the user eye based on the one or more glint positions relative to an eye part.

18. The system of claim 17 further comprising:

the one or more processors being communicatively coupled to the at least one image generation unit for controlling the at least one image generation unit for displaying the at least one virtual image at different locations in a user field of view viewable in the display device;

the at least one sensor capturing a calibration glint data set of intensity values for each glint during display of the at least one virtual image at each different location;

the one or more processors storing the calibration glint data sets of intensity values as indicators of calibration gaze vectors; and the one or more processors determining the gaze vector of the user eye based on comparisons of the captured glint data with the calibration glint data sets.

19. The system of claim 17 further comprising wherein the at least one sensor is a position sensitive detector and the one or more processors turns each illuminator on and off in a predetermined sequence for capturing one or more data sets of glint intensity values.

20. The system of claim 17 wherein the glint intensity data comprises one or more data sets of glint intensity values and the number of glints include at least two glints, and the one or more processors determining a gaze vector for the user eye based on the one or more glint positions relative to an eye part further comprises:

the one or more processors determining one or more glint positions relative to an eye part based on the glint intensity data, the respective predetermined position of each illuminator in the set of infra-red illuminators, and the at least one predetermined position of the at least one sensor for detecting the glints reflected from each eye, and the one or more processors determining one or more glint positions relative to an eye part based on the glint intensity data further comprises determining a reflectivity data value represented by each glint intensity value, and identifying a glint corresponding to the respective glint intensity value as being located on a sclera, an iris portion or a pupil portion based on the reflectivity data value represented by each glint intensity value.

\* \* \* \* \*